(12) United States Patent
Sapiro et al.

(10) Patent No.: US 11,580,874 B1
(45) Date of Patent: Feb. 14, 2023

(54) METHODS, SYSTEMS, AND COMPUTER READABLE MEDIA FOR AUTOMATED ATTENTION ASSESSMENT

(71) Applicant: Duke University, Durham, NC (US)

(72) Inventors: Guillermo Sapiro, Durham, NC (US); Geraldine Dawson, Durham, NC (US); Matthieu Bovery, Durham, NC (US); Jordan Hashemi, Durham, NC (US)

(73) Assignee: Duke University, Durham, NC (US)

( * ) Notice: Subject to any disclaimer, the term of this patent is extended or adjusted under 35 U.S.C. 154(b) by 497 days.

(21) Appl. No.: 16/678,789

(22) Filed: Nov. 8, 2019

Related U.S. Application Data

(60) Provisional application No. 62/757,226, filed on Nov. 8, 2018.

(51) Int. Cl.
*G09B 19/00* (2006.01)
*G06V 40/18* (2022.01)
*G06V 40/20* (2022.01)

(52) U.S. Cl.
CPC ............ *G09B 19/00* (2013.01); *G06V 40/18* (2022.01); *G06V 40/20* (2022.01)

(58) Field of Classification Search
CPC ......... G09B 19/00; G06V 40/18; G06V 40/20
See application file for complete search history.

(56) References Cited

U.S. PATENT DOCUMENTS

| | | | |
|---|---|---|---|
| 6,231,187 B1 * | 5/2001 | Munoz | A61B 3/113 351/209 |
| 9,530,080 B2 | 12/2016 | Glazer | |
| 9,767,349 B1 * | 9/2017 | Shreve | G06V 40/176 |
| 10,165,176 B2 | 12/2018 | Frahm et al. | |
| 11,158,403 B1 | 10/2021 | Sapiro et al. | |
| 2004/0210159 A1 | 10/2004 | Kibar | |
| 2008/0068186 A1 * | 3/2008 | Bonefas | G08B 21/06 340/575 |
| 2008/0227063 A1 | 9/2008 | Kenedy et al. | |

(Continued)

OTHER PUBLICATIONS

Adrien et al., "Autism and family home movies: preliminary findings," Journal of Autism and Developmental Disorders, vol. 21(1), pp. 43-49, (1991).

(Continued)

*Primary Examiner* — Ryan A Lubitz
(74) *Attorney, Agent, or Firm* — Jenkins, Wilson, Taylor & Hunt, P.A.

(57) ABSTRACT

The subject matter described herein includes methods, systems, and computer readable media for automated attention assessment. According to one method, a method for automated attention assessment includes obtaining head and iris positions of a user using a camera while the user watches a display screen displaying a video containing dynamic region-based stimuli designed for identifying a neurodevelopmental and/or psychiatric (neurodevelopmental/psychiatric) disorder; analyzing the head and iris positions of the user to detect attention assessment information associated with the user, wherein the attention assessment information indicates how often and/or how long the user attended to one or more regions of the display screen while watching the video; determining that the attention assessment information is indicative of the neurodevelopmental/psychiatric disorder; and providing, via a communications interface, the attention assessment information, a diagnosis, or related data.

18 Claims, 10 Drawing Sheets

(56) References Cited

U.S. PATENT DOCUMENTS

| | | | |
|---|---|---|---|
| 2009/0271740 | A1 | 10/2009 | Ryan-Hutton et al. |
| 2009/0285456 | A1 | 11/2009 | Moon et al. |
| 2012/0002848 | A1 | 1/2012 | Hill |
| 2012/0293773 | A1 | 11/2012 | Publicover et al. |
| 2012/0314045 | A1 | 12/2012 | Billard et al. |
| 2014/0153794 | A1 | 6/2014 | Varaklis et al. |
| 2014/0315168 | A1 | 10/2014 | Movellan et al. |
| 2015/0099946 | A1 | 4/2015 | Sahin |
| 2015/0282705 | A1 | 10/2015 | Avital |
| 2015/0288877 | A1 | 10/2015 | Glazer |
| 2016/0128617 | A1 | 5/2016 | Morris et al. |
| 2016/0309081 | A1 | 10/2016 | Frahm et al. |
| 2017/0046567 | A1 | 2/2017 | Hong et al. |
| 2017/0184846 | A1* | 6/2017 | Lu .................. G02B 27/017 |
| 2017/0206412 | A1* | 7/2017 | Kaehler ................ G06T 7/74 |
| 2017/0365101 | A1* | 12/2017 | Samec ................ G16H 50/20 |
| 2018/0098724 | A1 | 4/2018 | Lu et al. |
| 2019/0029585 | A1* | 1/2019 | Geva .................. A61M 21/00 |
| 2019/0089946 | A1* | 3/2019 | Watari ................ G06T 7/285 |
| 2019/0125180 | A1* | 5/2019 | Arnold .................. A61B 3/08 |
| 2019/0139438 | A1* | 5/2019 | Tu ........................ G09B 5/02 |

OTHER PUBLICATIONS

Adrien et al., "Early symptoms in autism from family home movies. Evaluation and comparison between 1st and 2nd year of life using I.B.S.E. scale," Acta Paedopsychiatrica, vol. 55, No. 2, pp. 71-75, (1992).

Aharon, et al., "K-SVD: An Algorithm for Designing Overcomplete Dictionaries for Sparse Representation," IEEE Trans Signal Process, vol. 54, No. 11, pp. 4311-4322 (2006).

Anzulewicz et al. "Toward the Autism Motor Signature: Gesture patterns during smart tablet gameplay identify children with autism," Sci Rep, vol. 6, pp. 31107-1-31107-13 (2016).

Arvin, M., "Navy Funds Autism-Screening App, Hoping for Help with PTSD", Artificial Intelligence Online. pp. 1-6 (Mar. 20, 2016).

Baltrusaitis et al. "Openface: An open source facial behavior analysis toolkit," IEEE Winter Conference on Applications of Computer Vision (WACV), p. 1-10 (2016).

Baltrusaitis et al. "Openface 2.0: Facial Behavior Analysis Toolkit," IEEE International Conference on Automatic Face and Gesture Recognition (2018).

Baranek, G.T., "Autism during infancy: a retrospective video analysis of sensory-motor and social behaviors at 9-12 months of age," Journal of Autism and Developmental Disorders, vol. 29, No. 3, pp. 213-224 (1999).

Baveye et al. "LIRIS-ACCEDE: A Video Database for Affective Content Analysis," IEEE Transactions on Affective Computing, vol. 6, pp. 43-55, 2015.

Bloch et al., "On the onset of eye-head coordination in infants," Behavioural Brain Research, vol. 49, No. 1, pp. 85-90 (1992).

Boujarwah, et al., "Understanding the challenges and opportunities for richer descriptions of stereotypical behaviors of children with ASD: a concept exploration and validation," Proceedings of the 12th International ACM SIGACCESS Conference on Computers and Accessibility (ASSETS '10), pp. 67-74, Orlando, Fla, USA (Oct. 2010).

Brisson et al. "Motor anticipation failure in infants with autism: a retrospective analysis of feeding situations," Autism, 16(4), pp. 420-429 (2012).

Bryson et al., "A prospective case series of high-risk infants who developed autism," (SpringerLink) Journal of Autism and Developmental Disorders, vol. 37, No. 1, pp. 12-24 (2007).

Bryson, et al., "The autism observation scale for infants: scale development and reliability data," (SpringerLink) Journal of Autism and Developmental Disorders, vol. 38, No. 4, pp. 731-738 (25 pages) (2008).

Campbell et al. "Computer Vision Analysis Captures Atypical Attention in Toddlers with Autism," Author manuscript, pp. 1-19 [Published in final edited form as: Autism, 23(3), pp. 619-628 (2019)].

Chang, et al., "LIBSVM: a library for support vector machines," ACM Trans Intelligent Systems and Technology, vol. 2, No. 3, pp. 1-39 (2011).

"Computer vision of facial dynamics in infants at risk for autism," Job offer listed on Euraxess, pp. 1-4 (2017) [Accessed online Aug. 14, 2020].

Commonly-Assigned, Co-pending U.S. Appl. No. 15/141,391 for "Methods, Systems, and Computer Readable Media for Automated Behavioral Assessment," (Unpublished, filed Apr. 28, 2016).

Commonly-Assigned, Co-pending U.S. Appl. No. 16/678,828 for "Methods, Systems, and Computer Readable Media for Conducting an Automatic Assessment of Postural Control of a Subject," (Unpublished, filed Nov. 8, 2019).

Constantino et al. "Infant viewing of social scenes is under genetic control and is atypical in autism," Author manuscript, pp. 1-41 [Published in final edited form as: Nature, vol. 547(7663), pp. 340-344, (2017)].

Cook et al. "Atypical basic movement kinematics in autism spectrum conditions," Brain, 136(Pt 9), pp. 2816-2824 (2013).

Dalal, et al., "Histograms of oriented gradients for human detection," Proceedings of the IEEE Computer Society Conference on Computer Vision and Pattern Recognition (CVPR '05), pp. 886-893, San Diego, USA, pp. 1-9 (Jun. 2005).

Dawson et al. "Case Study of the Development of an Infant with Autism from Birth to Two Years of Age," Author manuscript, pp. 1-14 [Published in final edited form as: J Appl Dev Psychol, 21(3), pp. 299-313 (2000)].

Dawson, K. Toth, R. Abbott, et al., "Early Social Attention Impairments in Autism: Social Orienting, Joint Attention, and Attention to Distress," Developmental Psychology, No. 40(2), pp. 271-283 (2004).

Dawson, G., "Early behavioral intervention, brain plasticity, and the prevention of autism spectrum disorder," Development and Psychopathology, vol. 20, No. 3, pp. 775-803 (2008).

Dementhon et al. "Model-Based Object Pose in 25 Lines of Code," International Journal of Computer Vision, 15(1), pp. 123-141 (1995).

Downing, et al., "Can the AOSI at nine months discriminate between infants at high or low risk for ASD?", International Meeting for Autism Research (IMFAR'11), San Diego, Calif, USA (2011).

Egger, et al. "Automatic emotion and attention analysis of young children at home: A ResearchKit autism feasibility study," npj Nature Digital Medicine, 20, pp. 1-10 (2018).

Elsabbagh, et al., "Visual orienting in the early broader autism phenotype: disengagement and facilitation," Journal of Child Psychology and Psychiatry and Allied Disciplines, vol. 50, No. 5, pp. 637-642 (2009).

Elsabbagh, et al., "Disengagement of Visual Attention in Infancy is Associated with Emerging Autism in Toddlerhood," Biological Psychiatry, vol. 74, noI. 3, pp. 189-194 (2013).

Esler et al. "The Autism Diagnostic Observation Schedule, Toddler Module: Standardized Severity Scores," Author manuscript, pp. 1-28, [Published in final edited form as J Autism Dev Disord, vol. 45(9), pp. 2704-2720 (2015)].

Esposito, et al., "Analysis of unsupported gait in toddlers with autism," Brain and Development, vol. 33, No. 5, pp. 367-373 (2011).

Everingham, et al., ""Hello! My name is . . . Buffy"—automatic naming of characters in TV video," Proceedings of the British Machine Vision Conference (BMVC '06), Edinburgh, UK (2006).

Flanagan et al. "Head Lag in Infants at Risk for Autism: A Preliminary Study," Am J Occup Ther, 66(5), pp. 577-585 (2012).

Li, et al., "Learning to predict gaze in egocentric video," Proceedings of the International Conference on Computer Vision (ICCV'13), Sydney, Australia (2013).

Freeth, et al., "The Influence of visual salienxcy on fixation patterns in individuals with autism spectrum disorders," Neuropsychologia, vol. 49, No. 1, pp. 156-160 (2011).

Goodwin, et al., "Automated detection of stereotypical motor movements," Journal of Autism and Developmental Disorders, vol. 41, No. 6, pp. 770-782 (2011).

Gouleme et al. "Postural Control and Emotion in Children with Autism Spectrum Disorders," Transl Neurosci, 8, pp. 158-166 (2017).

(56) References Cited

OTHER PUBLICATIONS

Gross, et al., "Multi-PIE," FG, 2010, pp. 807-813.

Guney, et al., "Cross-pose facial expression recognition," FG, pp. 1-6 (2013).

Hashemi, et al., "Computer vision tools for low-cost and non-invasive measurement of autism-related behaviors in infants," Autism Research and Treatment, 935686 (2014).

Hashemi, et al., "A computer vision approach for the assessment of autism-related behavioral markers," IEEE International Conference on Development and Learning and Epigenetic Robotics (ICDL), San Diego, CA, 2012, pp. 1-7 (2012).

Hashemi et al. "A scalable app for measuring autism risk behaviors in young children: A technical validity and feasibility study," MobiHealth, pp. 1-5 (2015).

Hastie, et al., "The Elements of Statistical Learning", Springer-Verlag (2009).

Howard, et al., "A comparison of intensive behavior analytic and eclectic treatments for young children with autism," Research in Developmental Disabilities, vol. 26, No. 4, pp. 359-383 2005.

Interview Summary corresponding to U.S. Appl. No. 15/141,391 dated Sep. 25, 2019.

Interview Summary corresponding to U.S. Appl. No. 15/141,391 dated Feb. 12, 2020.

Jeni et al. "Dense 3D Face Alignment from 2D Videos in Real-Time," 2015 11th IEEE International Conference and Workshops on Automatic Face and Gesture Recognition (FG), pp. 1-8, May 4-8, 2015, DOI: 10.1109/FG.2015.7163142, Date Added to IEEE Xplore: Jul. 23, 2015.

Jeni et al. "Person-Independent 3D Gaze Estimation Using Face Frontalization," 2016 IEEE Conference on Computer Vision and Pattern Recognition Workshops (CVPRW) DOI: 10.1109/CVPRW.2016.104.

Jones, et al., "Absence of Preferential Looking to the Eyes of Approaching Adults Predicts Level of Social Disability in 2-Year-Old Toddlers with Autism Spectrum Disorder," Archives of General Psychiatry, vol. 65, No. 8, pp. 946-954 (2008).

Jones et al., "Attention to Eyes is Present But in Decline in 2-6 Month-Olds Later Diagnosed with Autism," Nature, vol. 504, pp. 427-431 (2013).

Jones et al. "Reduced engagement with social stimuli in 6-month-old infants with later autism spectrum disorder: A longitudinal prospective study of infants at high familial risk," Journal of Neurodevelopmental Disorders, 8:7, pp. 1-20 (2016).

Kalal, et al., "Face-TLD: Tracking-Learning-Detection Applied to Faces," Proceedings of 2010 IEEE 17th International Conference on Image Processing (ICIP '10), Hong Kong, pp. 3789-3792 (Sep. 2010).

Kang et al. "Automated Tracking and Quantification of Autistic Behavioral Symptoms Using Microsoft Kinect," Stud Health Technol Inform, 220, pp. 167-170 (2016).

Klin, et al., "Visual Fixation Patterns During Viewing of Naturalistic Social Situations as Predictors of Social Competence in Individuals with Autism," Archives of General Psychiatry, vol. 59, No. 9, pp. 809-816 (Sep. 2002).

Klin et al. "Social visual engagement in infants and toddlers with autism: Early developmental transitions and a model of pathogenesis," Author manuscript, pp. 1-34 [Published in final edited form as: Neurosci BiobehavRev., No. 50, pp. 189-203 (2014)].

Kumano, et al., "Pose-invariant facial expression recognition using variable intensity templates," IJVC, vol. 83, No. 2, pp. 178-194 (2009).

Landry, et al., "Impaired disengagement of attention in young children with autism," Journal of Child Psychology and Psychiatry and Allied Disciplines, vol. 45, No. 6, pp. 1115-1122 (2004).

Losche, et al., "Sensorimotor and action development in autistic children from infancy to early childhood," Journal of Child Psychology and Psychiatry and Allied Disciplines, vol. 31, No. 5, pp. 749-761 (1990).

Lucas da Silva et al. "A Web-Based Application to Address Individual Interests of Children with Autism Spectrum Disorders," Procedia Computer Science, vol. 14, pp. 20-27, (2012).

Lucas da Silva et al. "Inducing behavior change in children with Autism Spectrum Disorders by monitoring their attention," Proceedings of the International Conference on Physiological Computing Systems, vol. 1, pp. 131-136 (2014).

Rice et al. "Parsing Heterogeneity in Autism Spectrum Disorders: Visual Scanning of Dynamic Social Scenes in School-Aged Children," Author manuscript, pp. 1-17 [Published in final edited form as J Am Acad Child Adolesc Psychiatry, 51(3), pp. 238-248 (2012)].

Robins et al., "Modified Checklist for Autism in Toddlers, Revised with Follow-Up (M-Chat-R/F)TM," www.mchatscreen.com, pp. 1-3 (2009).

Robins et al. "Validation of the Modified Checklist for Autism in Toddlers, Revised with Follow-up (M-Chat-R/F)," Pediatrics, No. 133(1), pp. 37-45 (2014).

Rudovic et al., "Personalized machine learning for robot perception of affect and engagement in autism therapy," Science Robotics, vol. 3:19, pp. 1-11 (2018).

Martin et al. "Objective measurement of head movement differences in children with and without autism spectrum disorder," Mol Autism, 9:14, pp. 1-10 (2018).

Marko et al. "Behavioural and neural basis of anomalous motor learning in children with autism," Brain, 138 (Pt 3): pp. 784-797 (2015).

Mannan, et al., "Automatic control of saccadic eye movements made in visual inspection of briefly presented 2-D images," Spatial vision, vol. 9, No. 3, pp. 363-386 (1995).

Metallinou et al. "Quantifying Atypicality in Affective Facial Expressions of Children With Autism Spectrum Disorders," Author Manuscript, pp. 1-12 [Published in final edited form as Proc (IEEE Int Conf Multimed Expo), 1-6 (2013)].

Moore, et al., "Local binary patterns for Multiview facial expression recognition," Computer Vision and Image Understanding, vol. 115, pp. 541-558 (2011).

Muratori, et al., "Early signs of autism in the first year of life," in Signs of Autism in Infants: Recognition and Treatment, pp. 46-62, Karnac, London, UK (2007).

Murias et al. "Electrophysiological Biomarkers Predict Clinical Improvement in an Open-Label Trial Assessing Efficacy of Autologous Umbilical Cord Blood for Treatment of Autism," Stem Cells Translational Medicine, 7, pp. 783-791 (2018).

Murphy-Chutorian, et al., "Head pose estimation in computer vision: a survey," PAMI, vol. 31, No. 4, pp. 607-626 (2009).

Nadig, et al., "A prospective study of response to name in infants at risk for autism," Archives of Pediatrics and Adolescent Medicine, vol. 161, No. 4, pp. 378-383 (2007).

Nichols, et al., "Social Smiling and its Components in High-risk Infant Siblings Without Later ASD Symptomatology," J Autism Dev Disord, vol. 44, No. 4, pp. 894-902 (2014).

Office Action corresponding to U.S. Appl. No. 15/141,391 dated Jun. 26, 2019.

Office Action corresponding to U.S. Appl. No. 15/141,391 dated Nov. 14, 2019.

Office Action corresponding to U.S. Appl. No. 15/141,391 dated May 18, 2020.

Osterling, et al., "Early recognition of children with autism: a study of first birthday home videotapes," Journal of Autism and Developmental Disorders, vol. 24, No. 3, pp. 247-257 (1994).

Owada et al. "Computer-analyzed facial expression as a surrogate marker for autism spectrum social core symptoms," Plos One, 13(1), pp. 1-16 (2018).

Ozonoff, et al., "A Prospective Study of the Emergence of Early Behavioral Signs of Autism", J Am Acad Child Adolesc Psychiatry, vol. 49, No. 3, pp. 256-266 (Mar. 2010).

Pierce et al. "Preference for Geometric Patterns Early in Life as a Risk Factor for Autism," Author manuscript, pp. 1-20 [Published in final edited form as: Archives of General Psychiatry, No. 68(1), pp. 101-109 (2011)].

Qiu, et al., "Domain adaptive dictionary learning," in ECCV, pp. 631-645 (2012).

(56) References Cited

OTHER PUBLICATIONS

Qiu et al. "Low-cost Gaze and Pulse Analysis using RealSense," MobiHealth, pp. 1-4 (2015).
Rehg, et al., "Decoding children's social behavior," CVPR, pp. 3414-3421 (2013).
Rodier, et al., "Converging evidence for brain stem injury in autism," Development and Psychopathology, vol. 14, No. 3, pp. 537-557 (2002).
Rudovic, et al., "Coupled Gaussian processes for pose-invariant facial expression recognition," PAMI, vol. 35, No. 6, pp. 1357-1369 (2013).
Sandbach, et al., "Static and dynamic 3D facial expression recognition: A comprehensive survey," Image and Vision Computing, vol. 30, No. 10, pp. 683-697 (2012).
Scott, E., "App aims for faster autism diagnosis," The Arizona Republic, pp. 1-3 (Apr. 13, 2013).
Shan, et al., "Facial expression recognition based on local binary patterns: a comprehensive study," Image and Vision Computing, vol. 27, pp. 803-816 (2009).
Shattuck, et al., "Timing of identification among children with an autism spectrum disorder: findings from a population-based surveillance study," Journal of the American Academy of Child and Adolescent Psychiatry, vol. 48, No. 5, pp. 474-483 (2009).
Shi et al. "Different Visual Preference Patterns in Response to Simple and Complex Dynamic Social Stimuli in Preschool-Aged Children with Autism Spectrum Disorders," PLOS One, No. 10(3), pp. 1-16 (2015).
Shic et al., "Limited Activity Monitoring in Toddlers with Autism Spectrum Disorder," Author manuscript, pp. 1-19 [Published in final edited form as: Brain Research, No. 1380, pp. 246-254 (2011)].
Silva et al. "Automated Evaluation System for Human Pupillary Behavior," Stud Health Technol Inform. 245, pp. 589-593 (2017).
Steakley, "Using Kinect cameras to automate autism diagnosis," SCOPE, scopeblog.stanford.edu, pp. 1-4 (2012) [Accessed online Aug. 14, 2020].
Taheri, et al., "Structure-preserving sparse decomposition for facial expression analysis," IEEE Trans Image Process, vol. 23, No. 8, pp. 1-12 (2013).
Tang, et al., "Non-frontal view facial expression recognition based on ergodic hidden markov model supervectors," in ICME, pp. 1202-1207 (2010).
Tassi, "Microsoft's Kinect Being Employed to Help Detect Autism Early," Forbes.com, pp. 1-3 (2012) [Accessed online Aug. 14, 2020].
Teitelbaum et al. "Movement analysis in infancy may be useful for early diagnosis of autism," Proc Natl Acad Sci USA, vol. 95(23), p. 13982-13987 (1998).
Tepper, et al., "Decoupled coarse-to-fine matching and nonlinear regularization for efficient motion estimation," in Proceedings of the 19th IEEE International Conference on Image Processing (ICIP '12), pp. 1517-1520, Orlando, Fla, USA (Oct. 2012).
Vatahska, et al., "Feature-based head pose estimation from images," in Proceedings of the 7th IEEE-RAS International Conference on Humanoid Robots (HUMANOIDS '07), pp. 330-335, Pittsburgh, PA, USA (Dec. 2007).
Wang et al., "Quantifying Facial Expression Abnormality in Schizophrenia by Combining 2D and 3D Features," IEEE, pp. 1-8 (2007).
Wright, et al., "Robust face recognition via sparse representation," IEEE Transactions on Pattern Analysis (PAMI), vol. 31, No. 2, pp. 1-18 (2009).
Wu et al. "A Biomarker Characterizing Neurodevelopment with applications in Autism," Scientific reports, 8:614, pp. 1-14 (2018).
Xiong, et al., "Supervised descent method and its applications to face alignment," CVPR, pp. 532-539, (2013).
Yandell, K., "Computer vision may aid in screening for autism," SFARI Simons Foundation Autism Research Initiative, p. 1 (Jul. 16, 2014).
Ye, Z., et al., "Detecting eye contact using wearable eye-tracking glasses," in Proceedings of the 14th International Conference on Ubiquitous Computing (UbiComp '12), pp. 699-704, Pittsburgh, Pa, USA (Sep. 2012).
Yin, et al., "A 3D facial expression database for facial behavior research," in FG, pp. 211-216 (2006).
Zappella et al. "What do home videos tell US about early motor and socio-communicative behaviours in children with autistic features during the second year of life—An exploratory study," Author Manuscript, pp. 1-18 [Published in final edited form as: Early Hum Dev, 91(10), pp. 569-575 (2015)].
Zeng, et al., "A Survey of Affect Recognition Methods: Audio, Visual, and Spontaneous Expressions," IEEE Transactions on Pattern Analysis and Machine Intelligence (PAMI), vol. 31, No. 1, pp. 39-58 (Jan. 2009).
Zhao, et al., "A unified probabilistic framework for automatic 3D facial expression analysis based on a bayesian belief inference and statistical feature models," Image and Vision Computing, vol. 31, No. 3, pp. 231-245 (2013).
Zhu, Z., et al., "Robust real-time face pose and facial expression recovery," CVPR, pp. 681-688, (2006).
Zwaigenbaum, et al., "Behavioral manifestations of autism in the first year of life," International Journal of Developmental Neuroscience, vol. 23, No. 2-3, pp. 143-152 (2005).
Heiser et al. "Objective measurement of hyperactivity, impulsivity, and inattention in children with hyperkinetic disorders before and after treatment with methylphenidate," Eur Child Adolesc Psychiatry, 13(2), pp. 100-104 (2004).
Hytonen et al. "Postural Control and Age," Acta Otolaryngol, 113(2), pp. 119-122 (1993).
Interview Summary corresponding to U.S. Appl. No. 15/141,391 dated Feb. 16, 2021.
Kirchner et al. "Autistic Symptomatology, Face Processing Abilities, and Eye Fixation Patterns," Journal of Autism and Developmental Disorders, 41(2), pp. 158-167 (2011).
Lim et al. "Effect of Visual Information on Postural Control in Adults with Autism Spectrum Disorder," J Autism Dev Disord, 49, pp. 4731-4739 (2019).
Reiersen et al. "Co-occurrence of Motor Problems and Autistic Symptoms in Attention-Deficit/Hyperactivity Disorder," J Am Acad Child Adolesc Psychiatry, 47(6), pp. 662-672 (2008).
Merin et al. "Visual Fixation Patterns during Reciprocal Social Interaction Distinguish a Subgroup of 6-Month-Old Infants At-Risk for Autism from Comparison Infants," J Autism Dev Disord, 37, pp. 108-121 (2007).
Minshew et al. "Underdevelopment of the postural control system in autism," Neurology, 63(11), pp. 2056-2061 (2004).
Morris et al. "Differences in the use of vision and proprioception for postural control in autism spectrum disorder," Neuroscience, 307, pp. 273-280 (2015).
Murias et al. "Validation of Eye-Tracking Measures of Social Attention as a Potential Biomarker for Autism Clinical Trials," Autism Res., No. 11(1), pp. 166-174 (2018a).
Norbury et al. "Eye-movement patterns are associated with communicative competence in autistic spectrum disorders," Journal of Child Psychology and Psychiatry, 50(7), pp. 834-842 (2009).
Notice of Allowance and Interview Summary corresponding to U.S. Appl. No. 15/141,391 dated Jun. 28, 2021.
Office Action corresponding to U.S. Appl. No. 15/141,391 dated Dec. 1, 2020.
Pelphrey et al. "Visual Scanning of Faces in Autism," Journal of Autism and Developmental Disorders, vol. 32, No. 4, pp. 249-261 (2002).
Swettenham et al. "The Frequency and Distribution of Spontaneous Attention Shifts between Social and Nonsocial Stimuli in Autistic, Typically Developing, and Nonautistic Developmentally Delayed Infants," Journal of Child Psychology and Psychiatry, vol. 39, No. 5, pp. 747-753 (1998).
Werner et al. "Brief Report: Recognition of Autism Spectrum Disorder Before One Year of Age: A Retrospective Study Based on Home Videotapes," Journal of Autism and Developmental Disorders, vol. 30, No. 2, pp. 157-162 (2000).

(56) References Cited

OTHER PUBLICATIONS

Campbell et al. "Use of a Digital Modified Checklist for Autism in Toddlers—Revised with Follow-up to Improve Quality of Screening for Autism," The Journal of Pediatrics, vol. 183, pp. 133-139 (2017).

Campbell et al. "Computer vision analysis captures atypical attention in toddlers with autism," Autism, vol. 23(3), pp. 619-628 (2018).

Chang et al. "Synthesis-based Low-cost Gaze Analysis," International Conference on Human-Computer Interaction, pp. 1-6, Jul. 2016.

Chawarska et al. "Decreased Spontaneous Attention to Social Scenes in 6-Month-Old Infants Later Diagnosed with Autism Spectrum Disorders," Biological Psychiatry, No. 74(3), pp. 195-203 (2013).

Dawson et al. "Children with Autism Fail to Orient to Naturally Occurring Social Stimuli," Journal of Autism and Developmental Disorders, vol. 28, No. 6, pp. 479-485 (1998).

De la Torre et al., "IntraFace," Author manuscript, pp. 1-30 [published in final edited form as: IEEE Int Conf Autom Face Gesture Recognit Workshops] (2015).

Esposito et al. "An exploration of symmetry in early autism spectrum disorders: Analysis of lying," Brain Dev, 31(2), pp. 131-138 (2009).

Fischler et al. "Random Sample Consensus: A Paradigm for Model Fitting with Applications to Image Analysis and Automated Cartography," Commun. ACM, vol. 24, No. 6, pp. 381-395 (1981).

Ghanouni et al. "Effect of Social Stimuli on Postural Responses in Individuals with Autism Spectrum Disorder," J Autism Dev Disord, 47(5), pp. 1305-1313 (2017).

Gima et al. "Early motor signs of autism spectrum disorder in spontaneous position and movement of the head," Exp Brain Res, 236(4), pp. 1139-1148 (2018).

Gotham et al. "The Autism Diagnostic Observation Schedule: Revised Algorithms for Improved Diagnostic Validity," Journal of Autism and Developmental Disorders, 37(4), pp. 613-627 (2007).

Hashemi et al. "Computer Vision Analysis for Quantification of Autism Risk Behaviors," IEEE Transactions on Affective Computing, pp. 1-12 (2018).

Office Action corresponding to U.S. Appl. No. 16/678,828 dated Jun. 8, 2022.

\* cited by examiner

METHODS, SYSTEMS, AND COMPUTER READABLE MEDIA FOR AUTOMATED ATTENTION ASSESSMENT

CROSS REFERENCE TO RELATED APPLICATIONS

This application claims the benefit of U.S. Provisional Patent Application Ser. No. 62/757,226, filed Nov. 8, 2018, the disclosure of which is incorporated herein by reference in its entirety.

TECHNICAL FIELD

The subject matter described herein relates generally to automated attention assessment. More particularly, the subject matter described herein includes methods, systems, and computer readable media for automated attention assessment.

BACKGROUND

Neurodevelopmental and/or psychiatric (neurodevelopmental/psychiatric) disorders affect many people throughout the world. Current estimates indicate that 1 in 9 children may have or develop a neurodevelopmental and/or psychiatric disorder, such as an autism spectrum disorder (ASD), an anxiety disorder, or attention deficient and hyperactivity disorder (ADHD). For example, ASD is associated with deficits in the processing of social information and difficulties in social interaction, and individuals with ASD exhibit atypical attention and gaze. Such deficits in attention are among the earliest symptoms of neuropsychiatric conditions and persist throughout life, and thus can assist in risk detection, diagnosis, and symptom monitoring throughout the lifespan. Traditionally, gaze studies have relied upon precise and constrained means of monitoring attention using expensive equipment in laboratories. Hence, current attention assessment techniques include barriers that prevent or hinder effective diagnosis and symptom monitoring in various conditions, e.g., natural settings.

SUMMARY

This summary lists several embodiments of the presently disclosed subject matter, and in many cases lists variations and permutations of these embodiments. This summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this summary or not. To avoid excessive repetition, this summary does not list or suggest all possible combinations of such features.

The subject matter described herein includes methods, systems, and computer readable media for automated attention assessment. In some embodiments, a method for automated attention assessment occurs at a computing platform including at least one processor and memory. The method includes obtaining head and iris positions of a user using a camera while the user watches a display screen displaying a video containing dynamic region-based stimuli designed for identifying a neurodevelopmental and/or psychiatric (neurodevelopmental/psychiatric) disorder; analyzing the head and iris positions of the user to detect attention assessment information associated with the user, wherein the attention assessment information indicates how often and/or how long the user attended to one or more regions of the display screen while watching the video; determining that the attention assessment information is indicative of the neurodevelopmental/psychiatric disorder; and providing, via a communications interface, the attention assessment information, a diagnosis, or related data.

A system for automated attention assessment is also disclosed. In some embodiments, the system includes a computing platform including at least one processor and memory. In some embodiments, the computing platform is configured for: obtaining head and iris positions of a user using a camera while the user watches a display screen displaying a video containing dynamic region-based stimuli designed for identifying a neurodevelopmental/psychiatric disorder; analyzing the head and iris positions of the user to detect attention assessment information associated with the user, wherein the attention assessment information indicates how often and/or how long the user attended to one or more regions of the display screen while watching the video; determining that the attention assessment information is indicative of the disorder; and providing, via a communications interface, the attention assessment information, a diagnosis, or related data.

The subject matter described herein may be implemented in software in combination with hardware and/or firmware. For example, the subject matter described herein may be implemented in software executed by a processor (e.g., a hardware-based processor). In one example implementation, the subject matter described herein may be implemented using a non-transitory computer readable medium having stored thereon computer executable instructions that when executed by the processor of a computer control the computer to perform steps. Exemplary computer readable media suitable for implementing the subject matter described herein include non-transitory devices, such as disk memory devices, chip memory devices, programmable logic devices, such as field programmable gate arrays, and application specific integrated circuits. In addition, a computer readable medium that implements the subject matter described herein may be located on a single device or computing platform or may be distributed across multiple devices or computing platforms.

As used herein, the term "node" refers to a physical computing platform including one or more processors and memory.

As used herein, the terms "function" or "module" refer to software in combination with hardware and/or firmware for implementing features described herein. In some embodiments, a module may include a field-programmable gate array (FPGA), an application-specific integrated circuit (ASIC), or a processor.

BRIEF DESCRIPTION OF THE DRAWINGS

The subject matter described herein will now be explained with reference to the accompanying drawings of which.

DETAILED DESCRIPTION

Figure 1:
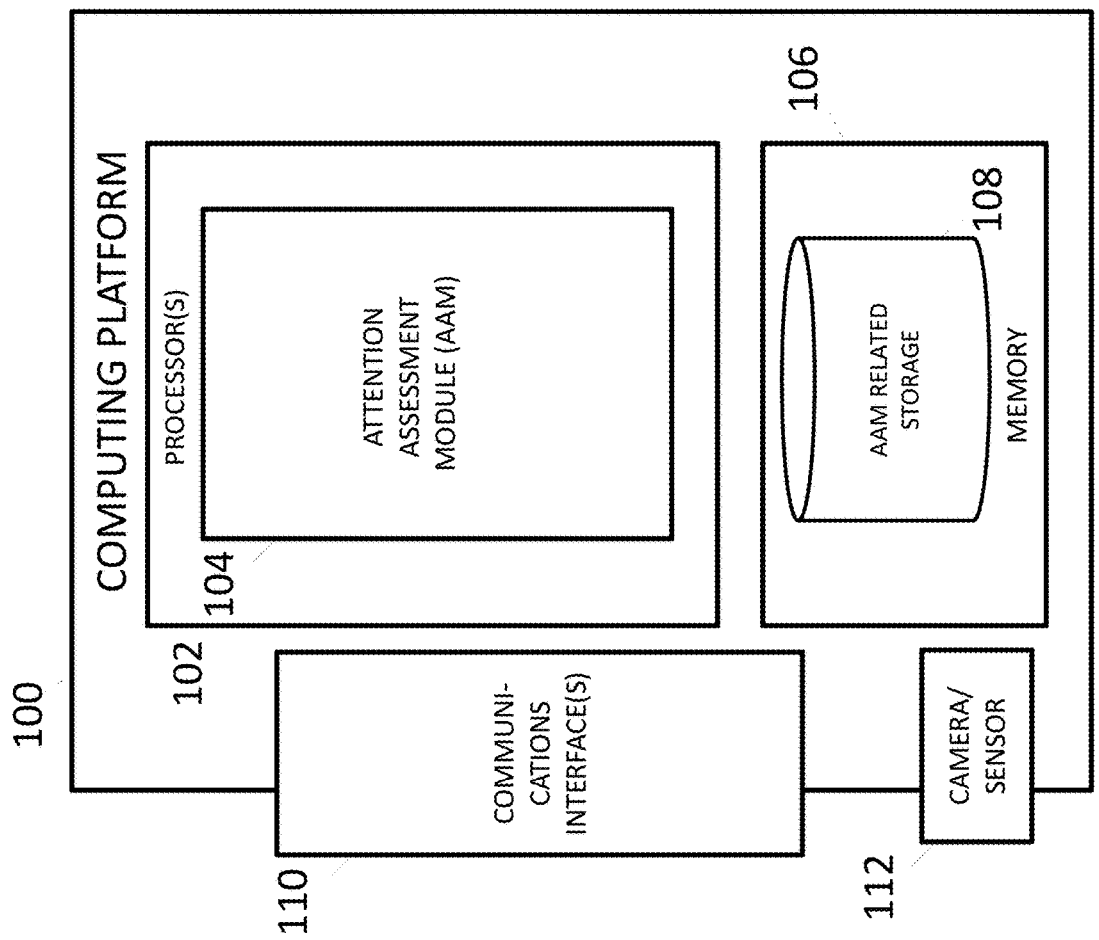
FIG. 1 is a diagram illustrating an example computing platform for automated attention assessment.

The subject matter described herein discloses methods, systems, and computer readable media for automated attention assessment. Autism spectrum disorder (ASD) is a neurodevelopmental disorder characterized by qualitative impairments in social interaction and the presence of restricted and repetitive behavior [1]. Studies of children in the first three years of life have shown that a failure to orient and lack of attentional preference for social information distinguishes children with ASD from those with typical development and other developmental delays [2], [3]. These atypical patterns of social attention are manifested early in life [4], [5], [6], and while not exclusive to ASD, are known to be strong candidates for ASD and developmental disorders biomarkers, even genetically influenced [7]. Thus, the development of feasible and reliable methods for detecting and monitoring early-emerging differences in patterns of attention is of significant interest, with the goal of eventually developing scalable behavioral analysis tools for early screening, diagnosis, and treatment monitoring.

Recognizing the importance of atypical attention as an early indicator of ASD, researchers have utilized eye-gaze tracking to measure gaze responses to dynamic visual stimuli. Such measures have been shown to differentiate ASD from other populations starting at the age of 6 months [8], [9], [10], [11], [12]. It has been demonstrated that children with ASD show differential gaze patterns compared to typically developing children, characterized by a lack of attention preference for socially salient stimuli [13], [14]. Some studies have shown that children with autism are less likely to shift their attention throughout the stimuli and explore scenes containing both social and non-social components [15]. These studies have used either expensive eye-tracking devices or advanced methods, such as dark pupil-corneal reflection video-oculography techniques, which are typically administered in a laboratory setting under a variety of constraints (specific lighting of the room, calibration procedures, minimal movement of the head during assessment). However, such sensing and acquisition approaches are not scalable and/or are not readily applicable in natural environments.

Various aspects of the present subject matter described herein relate to automated attention assessment or related tasks. In some embodiments, automated attention assessment may include gaze analysis (e.g., identifying and/or determining whether a user is viewing or watching one or more regions of a display screen) and may occur at or be performed by a module or an application (also referred to herein as "app") executing on a mobile device (e.g., a smartphone or a tablet device) or other computer (e.g., a server or computerized health related equipment).

In accordance with some aspects of the present subject matter, automated attention assessment and/or automated gaze analysis may be performed by one or more computing platforms. For example, a smartphone containing a camera may be usable to execute an attention assessment module that can provide stimuli, such as via a short (e.g., six minute) video, and can record user responses to the stimuli via the camera. In this example, the module or another entity (e.g., a communicatively coupled server) may be configured to process and/or analyze recorded responses and/or other information, e.g., by identifying and quantifying which regions of a display screen the user was looking at during the videos. Continuing with this example, attention assessment information may involve analyzing head and iris positions of a user for various temporal blocks (e.g., groups of related video frames) and using quantitative metrics associated with the attention assessment information to determine whether the attention assessment information is indicative of one or more neurodevelopmental and/or psychiatric (neurodevelopmental/psychiatric) disorders. The method anticipates that attention will be measured in natural environments that vary in background noise and light and that individuals with neurodevelopmental/psychiatric disorders will not be able to sit still, making it readily exportable to natural settings, such as homes and clinics.

In accordance with some aspects of the present subject matter, an automated attention assessment and/or tracking algorithm may utilize videos designed for presenting region-based stimuli for facilitating detection of a viewer's direction of attention. In some embodiments, a specially designed attention assessment video may include two or more screen regions, where each screen region may display a different type of stimuli. For example, a right side of an attention assessment video may include social stimuli like an actor looking toward and interacting with a viewer and a left side of the attention assessment video may include non-social stimuli like a visually interesting moving object. In this example, automated attention assessment and/or tracking algorithm may utilize the attention assessment video by performing a right versus left attention discrimination to assess a user's attention to social or non-social stimulus.

In accordance with some aspects of the present subject matter, an automated attention assessment and/or tracking algorithm may present a specially designed attention assessment video to a user via a mobile device or a display device and may use a camera (e.g., in the mobile device) to record the user's responses. In some embodiments, automated attention assessment and/or tracking algorithm may receive head position and eye position information (e.g., by processing the recorded user responses), and use the information to determine which part of the screen the user was looking at for one or more video frames.

By generating and/or utilizing videos containing region-based stimuli, an automated attention assessment and/or tracking algorithm in accordance with aspects described herein can perform various attention assessment related tasks with off-the-shelf equipment, e.g., a standard RGB camera and consumer-available processors. Moreover, by designing region-based stimuli that is compatible with an attention assessment device (e.g., a tablet with a front-facing camera), a scalable, off-the-shelf solution can be engineered to measure the same type of eye gaze biomarkers that previously required high-end eye-tracking devices.

Further, by providing techniques, mechanisms, and/or methods for automated attention assessments, diagnosis and/or treatment for various neurodevelopmental/neuropsychiatric disorders (e.g., an autism spectrum disorder (ASD), an anxiety disorder, or attention deficient and hyperactivity disorder (ADHD)) may be performed quickly and efficiently.

Moreover, by providing automated attention assessments using camera and/or software executing on mobile devices or other relatively inexpensive devices, cost barriers associated with diagnosis and/or treatment of neurodevelopmental/psychiatric disorders may be alleviated. Furthermore, using aspects of the present subject matter, diagnosis and/or treatment for many neurodevelopmental/psychiatric disorders in young children (e.g., ages 1-5) may be facilitated and/or improved over conventional methods, thereby allowing treatments, strategies, and/or intervention methods to be implemented more broadly and earlier than previously possible with conventional methods. Such methods also offer a platform for measuring changes in attention over time to assess the efficacy of treatments.

FIG. 1 is a diagram illustrating an example computing platform 100 for automated attention assessment. Computing platform 100 may be any suitable entity (e.g., a mobile device or a server) configurable for performing automated attention assessments via recording (e.g., video recording) users as they watch specially designed videos containing region-based dynamic stimuli (e.g., social stimuli in a left or up region of a display screen and non-social stimuli in a right or down region of the display screen) and automatically analyzing the head and/or eye positions for determining an attention assessment information (e.g., information indicating how often and/or how long a user attended to (e.g., payed attention to) one or more regions of the display screen while watching the video) or a diagnosis based on the attention assessment information. For example, computer platform 100 may include a memory and at least one processor for executing a module (e.g., an app or other software) for automated attention assessment. In this example, computer platform 100 may also include a user interface for providing a video containing region-based stimuli designed to identify a neurodevelopmental/psychiatric disorder in the viewer (e.g., a child, an adult, etc.) and a camera for recording the user and/or obtaining head and/or eye positions of the user during a video. Continuing with this example, the module executing at computing platform 100 may use recorded images or head and/or eye positions therefrom for determining attention assessment information related to the video and/or a related diagnosis (e.g., a diagnosis of a neurodevelopmental/psychiatric disorder or a related metric, such as a number between 0 and 10 indicating the likelihood of a user having a particular neurodevelopmental/psychiatric disorder).

Computing platform 100 may include processor(s) 102. Processor(s) 102 may represent any suitable entity or entities (e.g., one or more hardware-based processor) for processing information and executing instructions or operations. Each of processor(s) 102 may be any type of processor, such as a central processor unit (CPU), a microprocessor, a multi-core processor, and the like. Computing platform 100 may further include a memory 106 for storing information and instructions to be executed by processor(s) 102.

In some embodiments, memory 106 can comprise one or more of random access memory (RAM), read only memory (ROM), static storage such as a magnetic or optical disk, or any other type of machine or non-transitory computer-readable medium. Computing platform 100 may further include one or more communications interface(s) 110, such as a network interface card or a communications device, configured to provide communications access to various entities (e.g., other computing platforms). In some embodiments, one or more communications interface(s) 110 may be a user interface configured for allowing user (e.g., an attention assessment subject or an operator) to interact with computing platform 100 or related entities. For example, a user interface may include a graphical user interface (GUI) for providing a questionnaire to user and/or for receiving input from the user and/or for displaying region-based stimuli to a user. In some embodiments, memory 106 may be utilized to store an attention assessment module (AAM) 104, or software therein, and an AAM related storage 108.

AAM 104 may be any suitable entity (e.g., software executing on one or more processors) for performing one or more aspects associated with automated attention assessment. In some embodiments, AAM 104 may be configured for automated attention assessment. For example, AAM 104 may be configured for obtaining head and iris positions of a user using a camera while the user watches a display screen displaying a video containing dynamic region-based stimuli designed for identifying a neurodevelopmental/psychiatric disorder; analyzing the head and iris positions of the user to detect attention assessment information associated with the user, wherein the attention assessment information indicates how often and/or how long the user attended to one or more regions of the display screen while watching the video; determining that the attention assessment information is indicative of the neurodevelopmental/psychiatric disorder; and providing, via a communications interface, the attention assessment information, a diagnosis, or related data.

In some embodiments, computing platform 100 and/or AAM 104 may be communicatively coupled to a camera and/or a sensor (camera/sensor) 112. Camera/sensor 112 may represent any suitable entity (e.g., a camera sensor or camera chip in a smartphone) for recording visual images, audio, and/or other user input (e.g., motion). For example, camera/sensor 112 may include a two dimensional camera, a three dimensional camera, a heat-sensor camera, etc. In some embodiments, camera/sensor 112 may be usable for recording a user during an attention assessment (e.g., while the user is watch a video containing region-based stimuli).

In some embodiments, AAM 104 may obtain, from a recording, head and iris positions of a user using a camera (e.g., a front facing camera) while the user watches a video displaying stimuli in one or more regions of a display screen; analyzing the head and iris positions of the user to detect the direction of attention for one or more frames or groups of frames of the video; determining attention assessment information indicating the one or more regions of the display screen being attended to by the user for the one or more frames or groups of frames of the video; and determining that the attention assessment information is indicative of the neurodevelopmental/neuropsychiatric disorder (e.g., where the user pay less attention to the video compared to a baseline, shows less attention to the social stimuli or screen region as compared to the non-social stimulus or screen region compared to a baseline, and/or fixes their attention to one side of the screen).

In some embodiments, AAM 104 or a related entity (e.g., a medical provider) may administer to a user a therapy or therapies for treating a neurodevelopmental/psychiatric disorder. For example, after performing an attention assessment and/or a related diagnosis of a neurodevelopmental/psychiatric disorder, AAM 104 may provide one or more training programs for treating or improving attention in a user. In this example, the one or more training programs may be based on a number of factors, including user related factors, such as age, name, knowledge, skills, sex, medical history, and/or other information.

In some embodiments, AAM 104 may determine and/or provide attention assessment information, a diagnosis, and/or or related information (e.g., follow-up information and/or progress information) to one or more entities, such as a user, a system operator, a medical records system, a healthcare provider, a caregiver of the user, or any combination thereof. For example, attention assessment information, a diagnosis, and/or related information may be provided via a phone call, a social networking message (e.g., Facebook or Twitter), an email, or a text message. In another example, attention assessment information may be provided via an app and/or communications interface(s) 110. When provided via an app, attention assessment information may include progress information associated with a user. For example, progress information associated with a user may indicate (e.g., to a caregiver or physician) whether certain therapies and/or strategies are improving or alleviating symptoms associated with a particular neurodevelopmental/psychiatric disorder. In another example, progress information may include aggregated information associated with multiple videos and/or assessment sessions.

Memory 106 may be any suitable entity or entities (e.g., non-transitory computer readable media) for storing various information. Memory 106 may include an AAM related storage 108. AAM related storage 108 may be any suitable entity (e.g., a database embodied or stored in computer readable media) storing user data, stimuli (e.g., videos or video segments), recorded responses, and/or predetermined information. For example, AAM related storage 108 may include user data, such as age, name, knowledge, skills, sex, and/or medical history. AAM related storage 108 may also include predetermined information, including information gathered by clinical studies, patient and/or caregiver surveys, and/or doctor assessments. The predetermined information may include information for analyzing responses, information for determining based responses, information for determining assessment thresholds, coping strategies, recommendations (e.g., for a caregiver or a child), treatment and/or related therapies, information for generating or select videos, video segments or related stimuli for various screen regions usable for an automated attention assessment, and/or other information.

In some embodiments, AAM related storage 108 or another entity may maintain associations between relevant health information and a given user or a given population (e.g., users with similar characteristics and/or within a similar geographical location). For example, users associated with different conditions and/or age groups may be associated with different recommendations, base responses, and/or assessment thresholds for indicating whether user responses are indicative of neurodevelopmental/psychiatric disorders.

In some embodiments, AAM related storage 108 may be accessible by AAM 104 and/or other modules of computing platform 100 and may be located externally to or integrated with AAM 104 and/or computing platform 100. For example, AAM related storage 108 may be stored at a server located remotely from a mobile device containing AAM 104 but still accessible by AAM 104. In another example, AAM related storage 108 may be distributed or separated across multiple nodes.

It will be appreciated that the above described modules are for illustrative purposes and that features or portions of features described herein may be performed by different and/or additional modules, components, or nodes. For example, aspects of automated attention assessment described herein may be performed by AAM 104, computing platform 100, and/or other modules or nodes.

Figure 2:
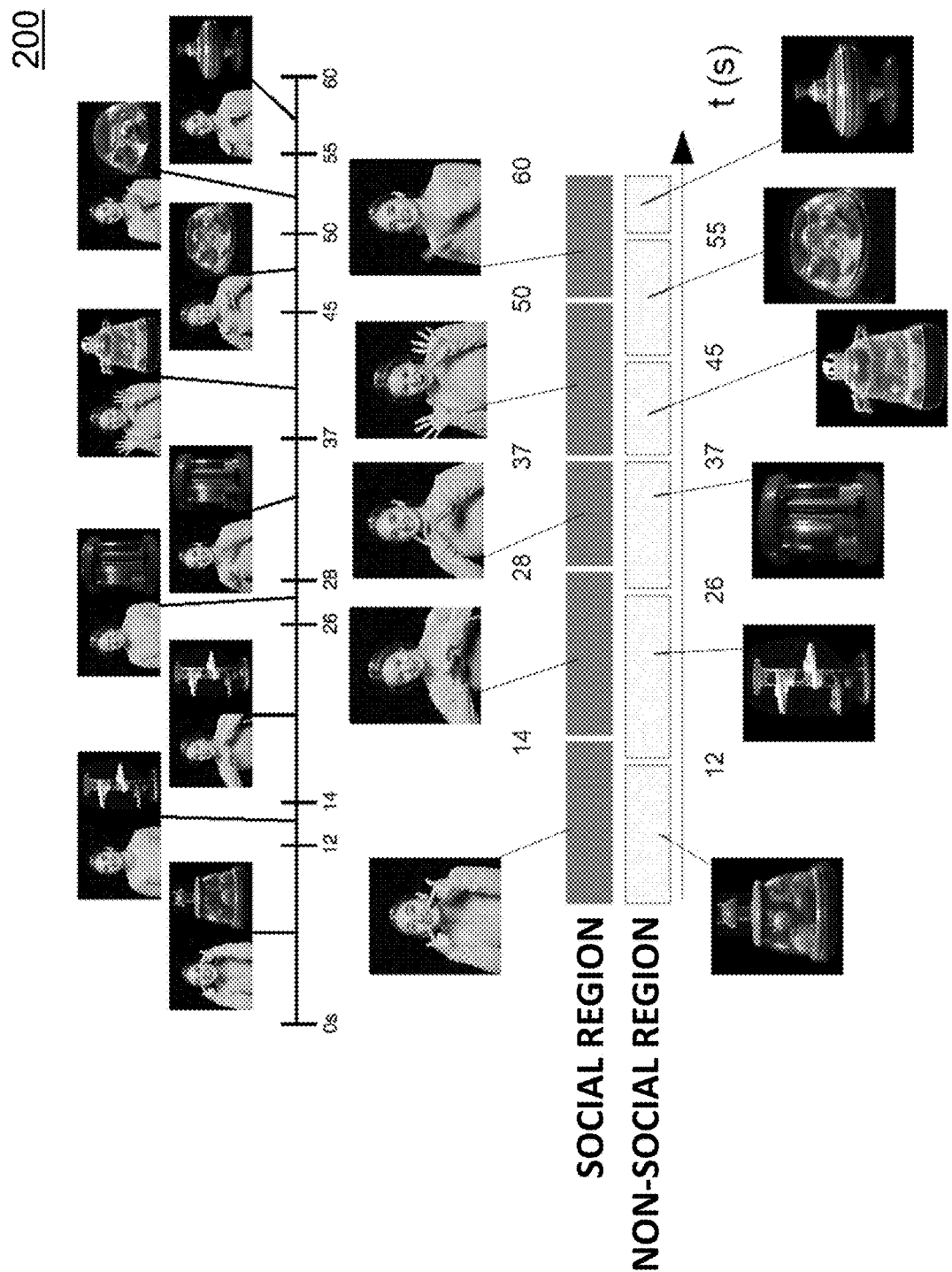
FIG. 2 is a diagram illustrating an example video for attention assessment.

FIG. 2 is a diagram illustrating aspects of an example video 200 for attention assessment. In some embodiments, video 200 may be specially designed to show different types of stimuli in two regions. For example, video 200 may include social stimuli on a right side of a display screen and non-social stimuli on a left side of a display screen. In another example, video 200 may include social stimuli on a top side of a display screen and non-social stimuli on a bottom side of a display screen.

Referring to FIG. 2, video 200 includes social stimulus (e.g., singing women) in one screen region and non-social stimuli (e.g., toys) in another screen region. Both screen regions may change stimuli during the duration of video 200, e.g., nine temporal blocks in 60 seconds. In some embodiments, video 200 may be carefully designed in an integrated fashion, e.g., by considering not only the type of stimuli but also the sensing device used to record viewer's responses (e.g., a regular camera) and capabilities of the automatic attention analysis algorithm.

In some embodiments, each of a plurality of regions in video 200 may show dynamic or changing stimuli. For example, a video may include temporal blocks that represent a number of video frames and may include a particular event, object, or actor. In this example, each region may have temporal blocks of varying lengths and may be similar to or different from the temporal blocks of other regions.

In some embodiments, video 200 may be displayable in landscape mode and split in two regions: on the left side a woman is singing to the child, and on the right side a moving toy making some noise to also try to draw the user's attention. The woman as well as the toy may change or move throughout the video.

In some embodiments, stimuli used in video 200 may be based on known examples or types of social and non-social stimuli, e.g., [9], [24], [25], [26]. The social and non-social regions may differ also in color and dynamics, and one may argue that this might influence the child's attention as well (and not just the social or non-social aspects of the regions). This influence, even if it exists, is not affecting an example computational approach described herein, since the goal is to detect the direction the user is looking at, regardless (at this stage) of the reason they are looking at it, and this is accomplished by the proposed algorithm described next. Moreover, regardless of the exact reason for the left-right attention preference, there is still a fundamental difference between ASD and non-ASD groups, as we will show in subsequent sections, providing potential value as a behavioral biomarker, for example for screening.

In some embodiments, social stimuli may involve cartoons, people, or other entities performing social activities, such as smiling, laughing, singing, or talking to the viewer. In some embodiments, non-social stimuli may involve visually stimulating (but non-social) scenes or objects. For example, a ball bouncing or toying spinning may be non-social stimulus.

In some embodiments, an automated attention assessment using video 200 may be performed at a clinic visit, a doctor's office, or at home. For example, during a regular clinic visit (no special setup, just a standard pediatric clinic room), a user (e.g., a child) may sit on a caregiver's lap while watching video 200 via a mobile device, e.g., a phone or tablet. In this example, the mobile device may be placed on a stand away from the user to prevent them from touching the screen. Continuing with this example, a front facing camera may record the user's face (e.g., at 1920×1080 and 30 frames per second resolution) while they were watching video 200, where the recording can be analyzed to measure attention.

Figure 3:
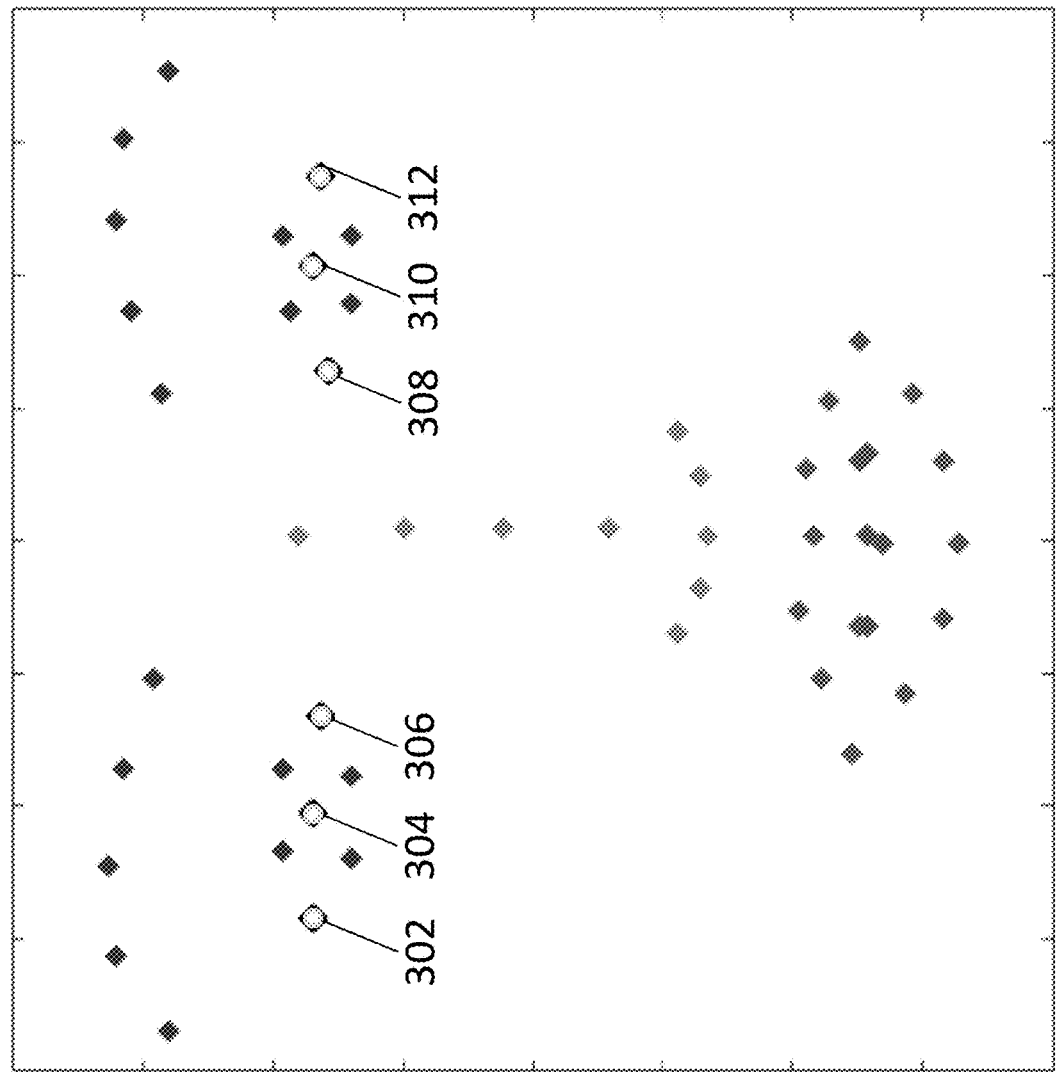
FIG. 3 is a diagram illustrating example facial landmarks.

FIG. 3 is a diagram illustrating example facial landmarks 300. In some embodiments, head position tracking may be performed using recorded video or images, e.g., captured by a camera associated with a mobile device. For example, a computer vision algorithm (CVA) detailed in [20] may automatically detect and track 51 facial landmarks 300 on a user's face, and which are usable for detection of head, mouth, and eye position [27].

In some embodiments, facial landmarks 300 or portions thereof may be usable for automated attention assessment using a computational algorithm as described herein. As depicted in FIG. 3, right eye right edge landmark 302 may represent a right most edge of a right eye, right pupil landmark 304 may represent the pupil of the right eye, and right eye left edge landmark 306 may represent a left most edge of the right eye. Similarly, left eye right edge landmark 308 may represent a right most edge of a left eye, left pupil landmark 310 may represent the pupil of the left eye, and left eye left edge landmark 312 may represent a left most edge of the left eye.

Various attention tracking or related assessment algorithms described herein may be based on region and not pixel accuracy and may be utilized when integrated with properly designed stimuli, thereby providing robustness (e.g., since accuracy needs to be region based on and not pixel based). Moreover, any further improvement in the landmarks detection (see for example [29], [30]) can be incorporated into an example framework described herein since these are usable as inputs in one or more algorithms described herein.

In some embodiments, head positions relative to a camera may be estimated by computing the optimal rotation parameters between the detected landmarks and a 3D canonical face model [31].

In some embodiments, an attention assessment and/or gaze tracking algorithm may track frame-by-frame the direction of a user's attention based on head and eye positions obtained from a recording of a user watching video 200. For example, for a given frame or group of frames, a tracking algorithm may determine that one or more regions of a plurality of potential screen regions were being attended to by a user (e.g., the viewer of the video) or the tracking algorithm may determine that no region was attended to by the user (e.g., the user did not watch video 200 at all).

Figure 4:
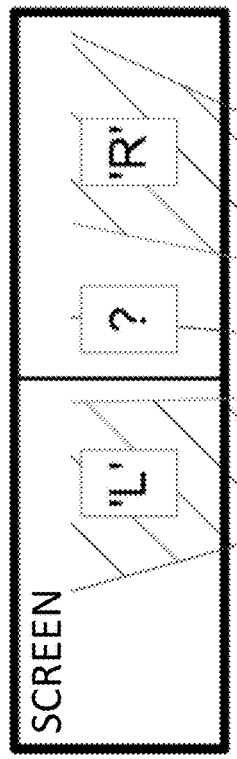
FIG. 4 is a diagram illustrating aspects of an example attention assessment and/or gaze tracking algorithm.
Figure 4:
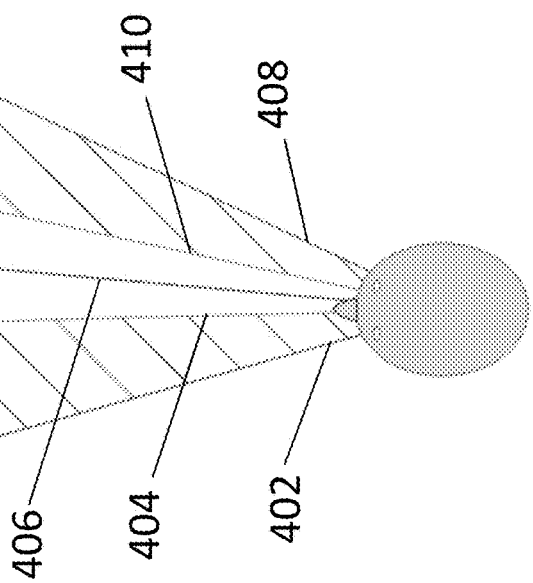

FIG. 4 is a diagram 400 illustrating aspects of an example attention assessment and/or gaze tracking algorithm. In some embodiments, an attention assessment and/or gaze tracking algorithm may be a CVA or other algorithm that utilizes various visual data points, landmarks, or related information. For example, an attention assessment and/or gaze tracking algorithm may utilize head positions and eye positions associated with a video recording of a user's head as they watch video 200. In this example, attention assessment and/or gaze tracking algorithm may also use landmarks (e.g., points in a video or image that can identify an object or a feature in the video or image) to detect gaze, direction of attention, or other relevant information.

In some embodiments, an attention assessment and/or gaze tracking algorithm may determine extreme yaw angle values associated with a user's detected head position. For example, line 402 may represent an extreme yaw angle value indicating an left, outermost line of vision and line 408 may represent an extreme yaw angle value indicating an right, outermost line of vision. The extreme yaw angles values (lines 402 and 408) may be used to determine the midrange yaw angle value (line 406) representing an approximate center of vision.

In some embodiments, an attention assessment and/or gaze tracking algorithm may determine thresholds values (lines 404 and 410) for identifying different regions. In some embodiments, a left (L) region and a right (R) region may be determined by adding or subtracting 10% of the difference between the midrange yaw angle (line 406) value and the extreme values (lines 402 and 408) to the midrange value. For example, line 404 may represent a value that indicates a right, outermost edge of the L region and line 410 may represent a value that indicates a left, outermost edge of the R region. With those thresholds determined, an attention assessment and/or gaze tracking algorithm may determine for a frame or group of frames whether a user is looking at the L region, at the R region, or inconclusive regarding direction of attention, e.g., the '?' region.

In some embodiments, when detecting a direction of attention, an attention assessment and/or gaze tracking algorithm may utilize one or more yaw angle values obtained from a user's head position. For example, for a given user, a midrange yaw angle value may be determined using an initial head position of the user (e.g., at start of video 200 or related assessment session) or an average midrange yaw angle value may be determined, e.g., based on head positions of the user during all the frames of video 200. In some embodiments, an attention assessment and/or gaze tracking algorithm may compare the difference between a yaw angle of a frame and a determined midrange yaw angle to the difference between the most extreme yaw angle value for the same frame and the determined midrange yaw angle. If the difference between the yaw angle and the determined midrange yaw angle value is at least 10% larger than the difference between the midrange yaw angle value and the extreme yaw angle value, an attention assessment and/or gaze tracking algorithm may determine an attention direction (provided that the difference is not too large to indicate no-attention, see [20]). For example, using thresholds values to distinguish regions, an attention assessment and/or gaze tracking algorithm may determine whether a user was looking at a particular region (e.g., a left or right side of a screen) based on the user's head position and associated yaw angle(s). In some embodiments, e.g., if an attention assessment and/or gaze tracking algorithm is unable to determine a direction of attention based on head position alone, eye landmarks 302-312 or other facial landmarks 300 may be used.

Figure 5:
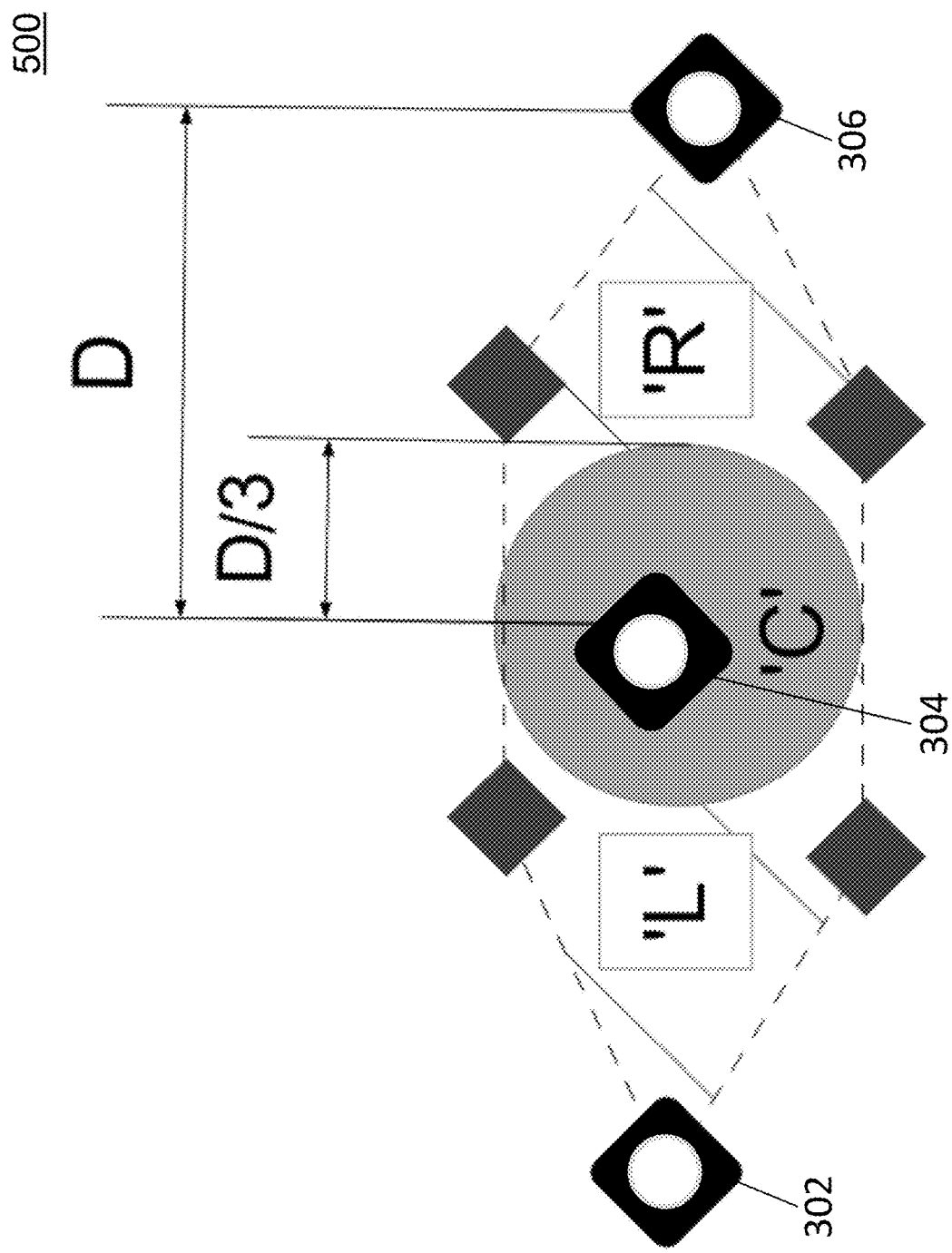
FIG. 5 is a diagram illustrating example eye landmarks and related measurements.

FIG. 5 is a diagram 500 illustrating example eye landmarks 302-306 associated with a right eye and related measurements. In some embodiments, an attention assessment and/or gaze tracking algorithm may determine a user's direction of attention by utilizing landmarks 302-306 representing points associated with the user's right eye. For example, eye edge landmarks 302 and 306 indicate the edges of the right eye and pupil landmark 304 indicates the pupil (e.g., center of the iris) of the right eye. In this example, an attention assessment and/or gaze tracking algorithm may estimate the middle of the eye based on eye edge landmarks 302 and 306 and may compute the distance (D) between the estimated middle of the eye and an eye edge (e.g., eye edge landmark 306).

In some embodiments, an attention assessment and/or gaze tracking algorithm may determine a user's direction of attention by determining whether pupil landmark 304 is close enough to one of the edges to determine the user's direction of attention. In such embodiments, determining whether pupil landmark 304 is close enough may involve determining whether the distance between pupil landmark 304 and the estimated center of the eye is greater than D/3.

If the distance between pupil landmark 304 and the estimated center of the eye is greater than D/3, an attention assessment and/or gaze tracking algorithm may determine a user's direction of attention. If not, an attention assessment and/or gaze tracking algorithm may determine a user's direction of attention is inconclusive or that the user is looking somewhere in the middle of the L and R regions, e.g., a center ('C') region.

In some embodiments, an attention assessment and/or gaze tracking algorithm may determine a user's direction of attention based one or both eyes. For example, an attention assessment and/or gaze tracking algorithm may compare position of each iris to one edge of a respective eye. In this example, if both irises were close enough to their respective edge (e.g., the distance between an iris and the center of an eye is larger than one third of the distance between the middle of the eye and either edge of the same eye), the attention assessment and/or gaze tracking algorithm may determine the user's direction of the attention (gaze) is conclusive. In some embodiments, the distances and the values used to determine whether an iris is close enough to the edge of an eye may be adjustable per-user and/or based on various factors, including user, robustness, and/or operator preferences.

In some embodiments, an attention assessment and/or gaze tracking algorithm may detect when a user's direction of attention cannot be determined or when the user's is not looking at a region of video 200. For example, an attention assessment and/or gaze tracking algorithm may fail to properly track eye landmarks 302-312 due to the user not facing the camera for one or more video frames. In this example, the algorithm may output non-numerical data and may associate those frames with a 'Not a Number' (NaN) value. In another example, an attention assessment and/or gaze tracking algorithm may assume a user is looking in the middle (center) of video 200 (e.g., between regions containing stimuli) when neither the value of a detected yaw angle associated with a user's head position nor the positions of the irises within the eyes are sufficient to conclude the user's direction of attention.

In some embodiments, an attention assessment and/or gaze tracking algorithm may perform temporal block analysis. For example, video 200 may be segmented into temporal blocks, where each temporal block may represent a number of consecutive video frames and may be related to a same stimulus. In this example, each region of video 200 may have a different number of temporal blocks and/or temporal blocks of varying lengths. Continuing with this example, an attention assessment and/or gaze tracking algorithm may detect or assess attention fixation or user responses to changes in stimuli by using temporal block analysis.

In some embodiments, temporal block analysis may involve determining shifts in attention when there is a change in either the social or the non-social stimuli (e.g., stimuli in both regions may not always change simultaneously). For example, boundaries of each temporal block may be based on a dynamic change of the toy (non-social), an actor (social), or both.

In some embodiments, for a given temporal block, an attention assessment and/or gaze tracking algorithm may determine a user's direction of attention by determining which direction or region the user is attending to for the majority of total frames (or total frames that are determinable for attention directions) within the temporal block. For example, assume a first temporal block has 600 frames and that an attention assessment and/or gaze tracking algorithm determines that for 400 frames of the 600 frames the user is paying attention to the R region, for 160 frames of the 600 frames the user is paying attention to the L region, and for 40 frames of the 600 frames the user's direction of attention is inconclusive. In this example, the user is paying attention to the R region for more than half of the first temporal block, the attention assessment and/or gaze tracking algorithm may determine that the user is paying attention to the R region during the first temporal block.

In some embodiments, an attention assessment and/or gaze tracking algorithm may provide attention assessment information at various granularities, such as by reporting a user's direction of attention per temporal block, e.g., categorized as 'L', 'R', 'C,' and 'NaN' for each temporal block in video 200. In some embodiments, reporting a user's direction of attention may be per frame, per stimulus, per stimulus type, or per region.

Figure 6:
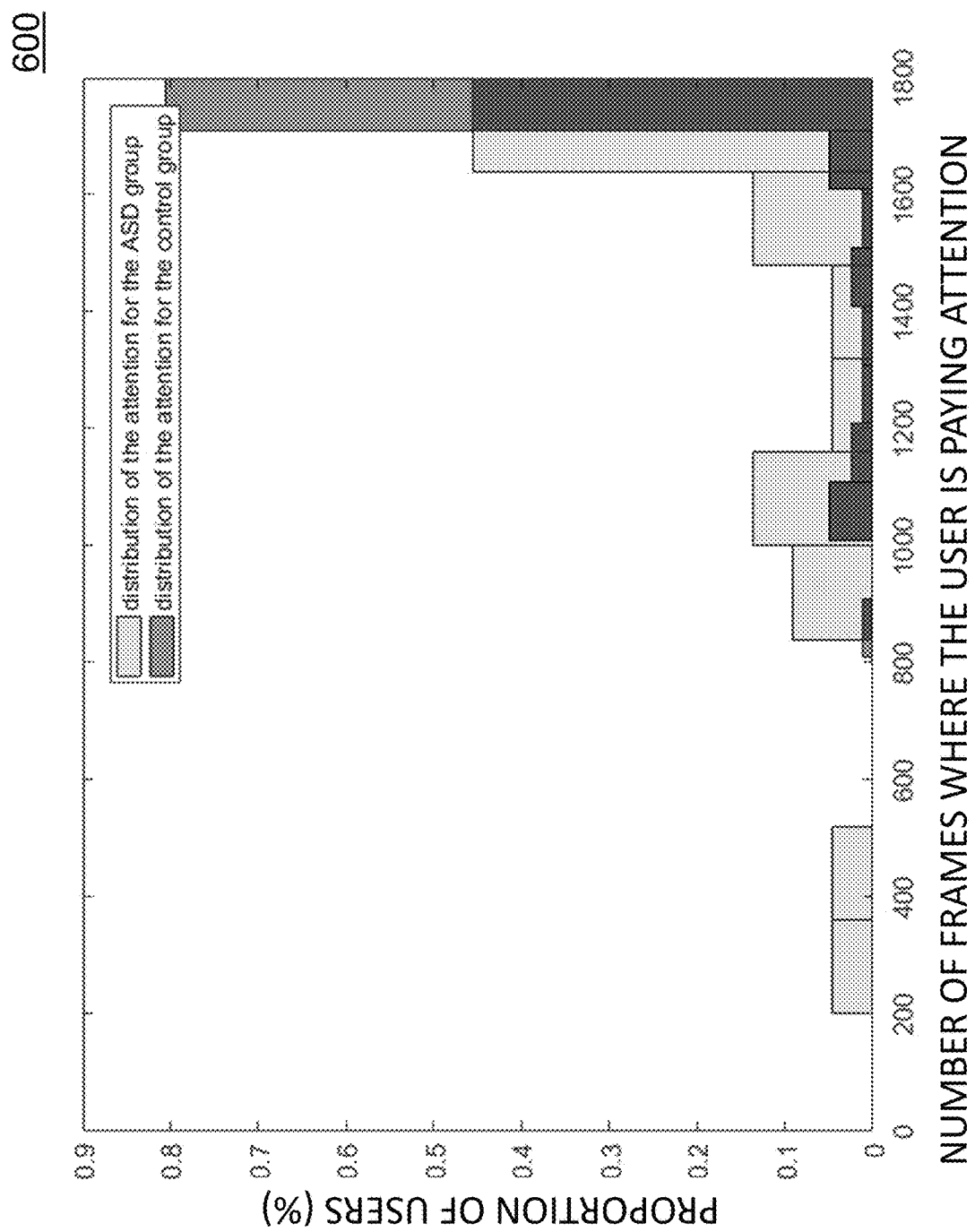
FIG. 6 is a diagram illustrating an amount of attention being paid by an autism spectrum disorder (ASD) group and a control group.

FIG. 6 is a diagram 600 illustrating an amount of attention being paid by an ASD group and a control group in a study using an example attention assessment framework and/or algorithm. Referring to FIG. 6, the vertical axis of diagram 600 may represent a proportion of users in the ASD group (colored light gray) and control group (colored dark gray) paying attention to the total number of movie frames as indicated in the horizontal axis. As depicted, diagram 600 uses defined attention frames which are the frames labeled either or 'C'.

In diagram 600, for the ASD group, the mean value was M=1,406 frames, and the standard deviation σ=460.3 frames. In comparison, M=1,717 frames and σ=228.3 frames for the control group. The number of users who were paying attention to fewer than 1,000 frames is 18.2% for the ASD group, whereas it was only 1% for the control group. About 74.4% of the control users were paying attention to the whole movie, while about 68.2% of the users with ASD were not attending at some point of the movie.

Figure 7:
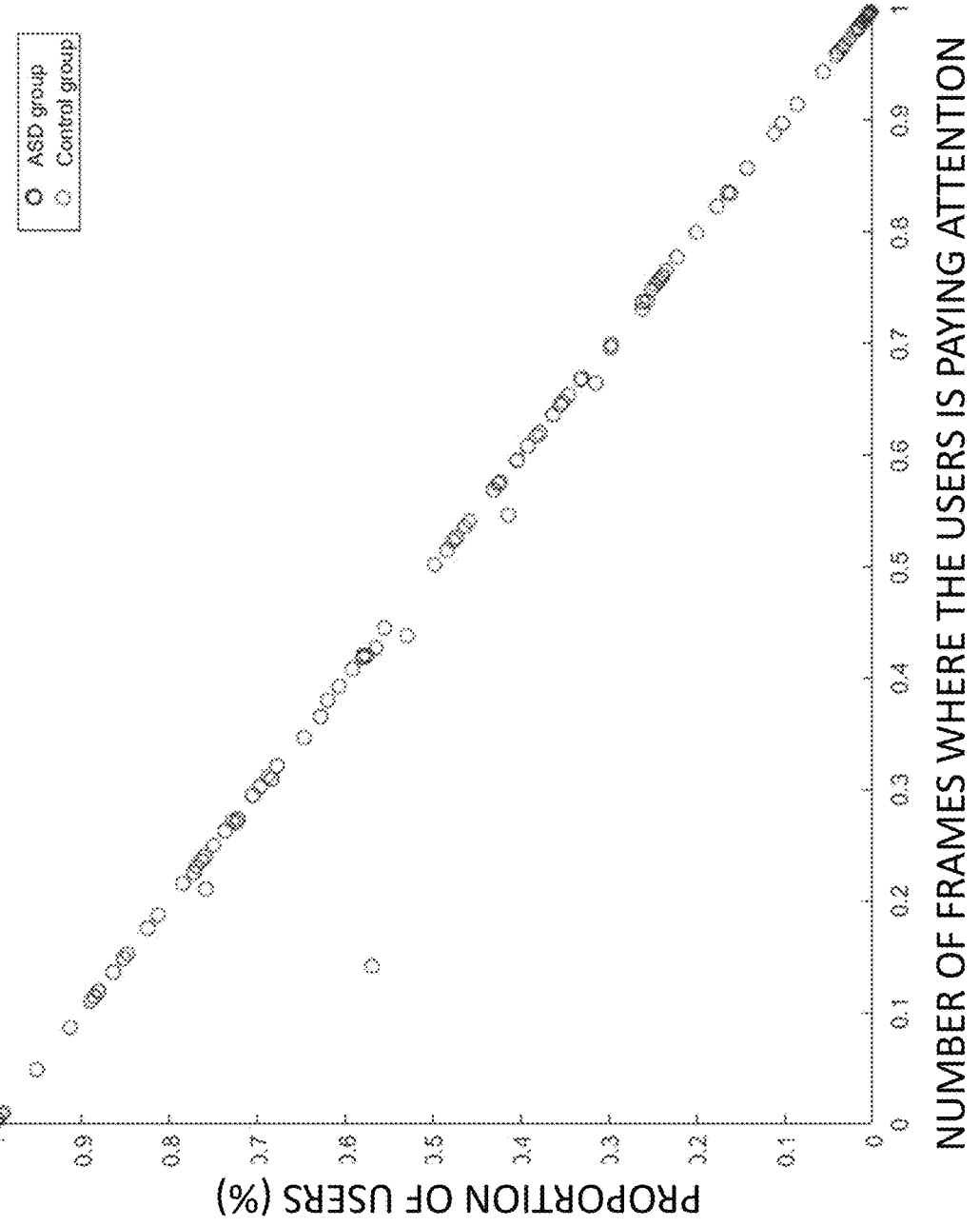
FIG. 7 is a diagram illustrating the ratio between attention to social stimuli and non-social stimuli for an ASD group and a control group.

FIG. 7 is a diagram 700 illustrating the ratio between attention to social stimuli and non-social stimuli for an ASD group and a control group in a study using an example attention assessment framework and/or algorithm. Referring to diagram 700, each user in the ASD group is depicted as a dark grey circle and each user in the control group is depicted as a light grey circle. As illustrated in FIG. 6, the proportion (%) of frames during which the users was looking right (non-social), as a function of the proportion (%) of frames during which the users was looking left (social stimulus) is shown. The proportions in diagram 700 were calculated by dividing the number of frames during which the users was looking at the given stimuli by the total amount of frames during which the user was paying attention. The pattern shown in FIG. 6 suggests that users with ASD and non-ASD users were attending to the movie in very similar ways. The means and standard deviations for attention to social stimulus were M=52%, σ=35% for the ASD group and M=55%, σ=29% for the control group. For the non-social stimulus, results were M=48%, σ=35% for the ASD group and M=44%, σ=29% for the control group. However, when the extreme values are examined, an interesting pattern emerged, a feature that distinguished ASD from non-ASD users is revealed. First, the proportion of users who paid attention to the social stimulus for greater than 95% of frames was similar across groups, 18% for the ASD group and 15% for the control group. In contrast, the proportion of users who paid attention to the non-social stimulus for greater than 90% of frames was 18% for the ASD group compared to only 2% for the control group, indicating that it is very rare for non-ASD users to spend most of their attention time on the non-social stimulus. Some points in FIG. 6 are not on the diagonal, indicating that those users are looking at the center of the stimuli for a significant number of frames. Almost 95% of the users devoted less than 1% of their attention to the center of the stimuli. Out of the 5% that did not, all were within the control group.

Figure 8:
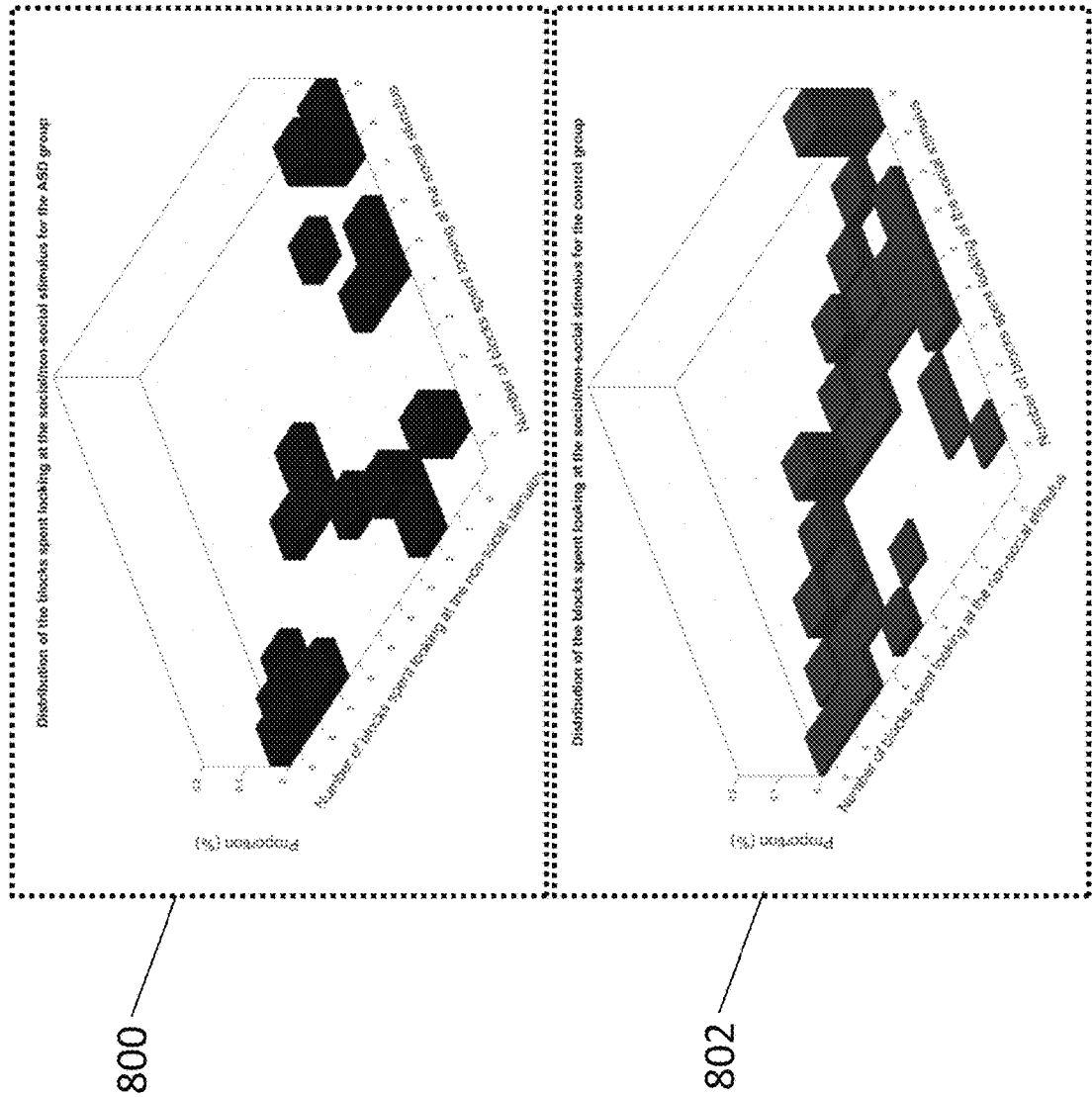
FIG. 8 is a diagram illustrating histograms depicting attention information for an ASD group and a control group.

FIG. 8 is a diagram illustrating histograms 800 and 802 depicting attention information for an ASD group and a control group in a study using an example attention assessment framework and/or algorithm. Each of histograms 800 and 802 is a three dimensional (3D) histogram show temporal patterns of attention direction taking into account the temporal block data, e.g., changes in the stimuli, where histogram 800 depicts information about the ASD group and histogram 802 depicts information about the control group.

Histograms 800 and 802 show temporal attention direction for nine different temporal blocks of video 200 resulting from the stimulus changing (see FIG. 2). For example, histograms 800 and 802 indicate how the different users spent their attention for each one of the nine temporal blocks of video 200, meaning each entry (i,j) represents the proportion of users spending i blocks attending to the left and j blocks attending to the right. Each value in the histogram position (i,j) (i,j=1 . . . 9) represents the percentage of users in the group that spent i temporal blocks attending to the left and j blocks attending to the right.

Referring to histogram 800, for the ASD group, only 28% of the points are located on the diagonal (meaning only 28% of the users are fully attending). More than 36.4% of the users have at least 8 out of their 9 blocks labeled either 'L' or 'R,' and 77% of them have less than two blocks labeled 'R' or less than two blocks labeled 'L'. Moreover, 59% of the users with ASD have less than one block labeled 'R' or less than one block labeled 'L.' All these results indicated a very one-sided attention orientation. The mean number of blocks spent looking at the social stimulus was M=3.3 blocks and the standard deviation σ=3.2 blocks. The mean number of blocks spent looking at the non-social stimulus was M=3.1 blocks and σ=3.3 blocks.

Referring to histogram 802, for the control group, 60% of the points are on the diagonal (points that add to 9, the total number of temporal blocks), which means those non-ASD users have their nine blocks labeled either 'L' or 'R.' Alongside the diagonal, the points are uniformly distributed, if not for two spikes. The one on right corresponds to the 15.8% users that have all their blocks labeled 'L.' The other one in the center corresponds to the 11° A of the users that have 4 blocks labeled 'L' and 5 blocks labeled 'R.' The mean value for the number of temporal blocks spent looking at the social stimuli is M=4.7 blocks and the standard deviation σ=2.8 blocks. For the number of blocks spent looking at the non-social stimuli, M=3.2 blocks and σ=2.7 blocks.

Figure 9:
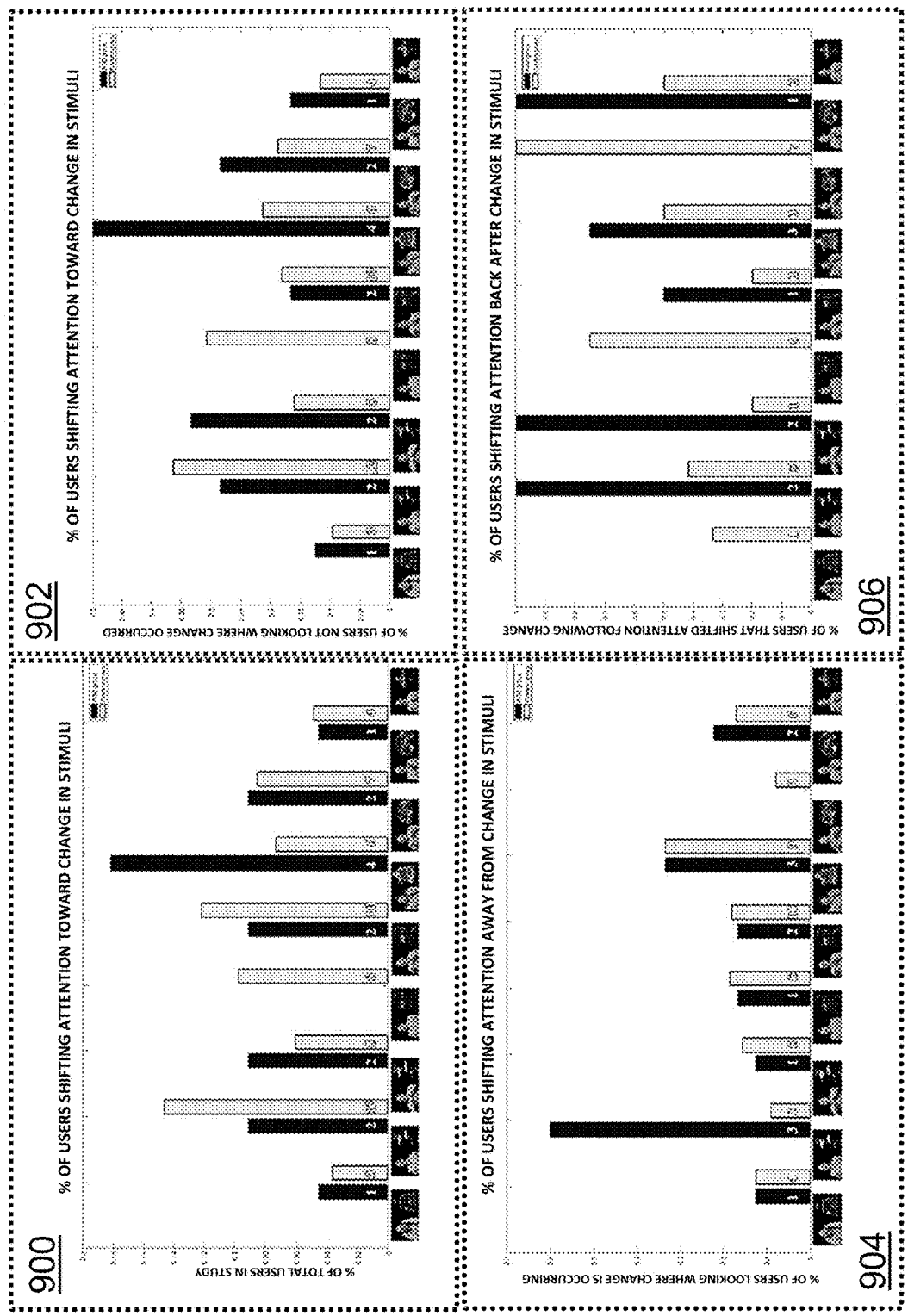
FIG. 9 is a diagram illustrating charts related to attention shifting for an ASD group and a control group.

FIG. 9 is a diagram illustrating charts 900-906 related to attention shifting for an ASD group and a control group in a study using an example attention assessment framework and/or algorithm. As shown in FIG. 2, the social stimuli changes 4 times (intervals 2-3, 4-5, 5-6, 7-8), while the non-social stimuli changes 5 times (intervals 1-2, 3-4, 5-6, 6-7, 8-9); these are indicated in the horizontal axis of each one of charts 900-906 in FIG. 9.

When referring to charts 900-906, assume that the stimuli change is happening in the left region of video 200. Chart 900 shows the percentage of users that shifted their attention toward the side where the change is happening, normalized by all the users. For example, chart 900 shows users that were looking at a right region and then looked at a left region when the change of stimuli happens divided by all users.

Chart 902 shows the percentage of users that shifted their attention toward the side where the change is happening, normalized by the users that were looking in the direction opposite to where the change happened. For example, chart 902 shows users that were looking at a right region and then looked at a left region when the change of stimuli happens divided by the users that were looking at the right region.

Chart 904 shows the percentage of users that were looking where the change happened and that shifted their attention away from the change of stimuli when it happened, normalized by the users that were looking where the change happened. For example, chart 904 shows users that were looking at a left region and then looked at a left region when the change of stimuli happens divided by the users that were looking at the left region.

Chart 906 shows the percentage of users that shifted their attention to where the change happened, but then shifted their attention back away from it, normalized by the users that shifted their attention to the region where the change happened. For example, chart 906 shows users that were looking at a right region, then looked at a left region when the change of stimuli happens, and then looked back at the right region divided by the users that were looking at the right region and then looked at the left region.

While the total number per class/stimulus switch is relatively small (indicated by the numbers in each bar) to perform full statistical analysis, an interesting pattern appears depending on what region, left/social or right/non-social changed.

Hence, an example attention assessment framework and/or algorithm described herein can provide information about granular and dynamic shifts of attention. Further, such a framework can perform attention with significantly less expensive components than conventional frameworks, thereby providing a low-cost scalable tool and paradigm to measure and/or assess attention.

Based on one or more studies utilizing an example attention assessment framework and/or algorithm described herein, a hypothesis that children with ASD differ from non-ASD children in terms of their overall attention to a presented video containing region-based stimuli was evaluated. For example, for each child in a study, an example attention assessment algorithm computed, frame by frame, whether or not the child was looking at a display screen showing video 200, and the number of frames during which the child was looking at the screen across the ASD group and the control group (FIG. 6). Based on the attention assessment data gathered in the study, the hypothesis that children with ASD exhibited reduced attention to the video overall was supported and was further supported with the block analysis (FIG. 8), where the density of points close to the origin (the beginning of the video) is significantly higher for the ASD group than it is for the control group. Those points are indicating that the child had most of their blocks labeled 'NaN,' which means that the child was not attending to the screen over multiple periods of time.

The results from the one or more studies also demonstrate the usefulness of low cost ubiquitous devices, consumer cameras available on tables or mobile phones, to measure attention. Such a framework is in sharp contrast with the high-end and expensive hardware that is common in most ASD studies. Secondly, these results can be informative as one feature that could contribute to an algorithm/scoring for ASD screening. For example, an example framework or system as described herein may identify that a user paying attention to less than a certain percentage of frames would be one feature more commonly associated with ASD. Using study data, for example, considering 1,000 frames, the values of the precision, recall and F1-score are P=0.8, R=1, and F1=0.89, respectively. These results are only a first step, and their statistical power needs to be investigated with larger populations. In addition, lack of attention is not an ASD exclusive behavior, and as such it should be considered as one of many scores in a full evaluation, similarly to the current standard of care which includes the observation of multiple behaviors.

Based on one or more studies utilizing an example attention assessment framework and/or algorithm described herein, a hypothesis that the ASD group attended more to the non-social than the social stimulus as compared to the control group was evaluated. For example, for each child in a study, an example attention assessment algorithm tracked attention on a frame-by-frame basis. The proportion of frames spent looking at the right, where the non-social part of the stimulus was displayed, versus the proportion of frames spent looking at the left, where the social part of the stimulus was displayed was examined and/or analyzed (FIGS. 1 and 4). U)sing the study data, analyses comparing the average number of frames looking at the social versus non-social stimuli did not yield group differences. However, analyses may be further improved by splitting the stimuli regions of video 200, e.g., in 4 (sub-)regions instead of just 2, and looking within the social stimuli to test if the ASD users are less likely to look at the face of the woman (e.g., a top part of a left side of video 200 or a related display screen), as suggested by earlier studies [35], [36], [8]. In some embodiments, an example framework or system as described herein can provide and support a number of regions (e.g., greater than two) with such increased accuracy using various computer vision tools (e.g., cameras, mobile devices, algorithms, etc.) described herein.

The one or more studies also reveal interesting results when looking at the extreme values with respect to how attention was distributed across the social and non-social stimuli. For example, when a user with ASD paid the majority of their attention to only one side of the screen, it was equally likely to be toward the social or non-social region. On the other hand, if a control user exhibited the same behavior of attending mostly one side of the screen, it was seven times more likely that the user was looking at the side of the screen displaying the social stimulus. This feature could also potentially be used as an additional risk marker for ASD by an example attention assessment device or module. These results and data also showed that a very high percentage of users with ASD focus almost solely on a single side of the screen and were less likely to switch their attentional focus from one side to the other.

Based on one or more studies utilizing an example attention assessment framework and/or algorithm described herein, attention fixation behavior (e.g., the degree to which a user shifts their attention from one region to another region throughout video 200) was evaluated. As shown in FIG. 2, video 200 used in a study was divided into temporal blocks corresponding to different social or non-social stimuli. The most popular label over each temporal block was determined and the corresponding per-block frequencies were computed (FIG. 8). By analyzing the users that are paying attention to most of the stimulus, that is, the points that are close to the diagonal in the 3D histograms, various patterns are distinguishable between the ASD and the control groups. The non-ASD children follows two main patterns: while some of the children spent most of the time attending the social stimulus, most distributed their attention between both the social and the non-social ones. The vast majority of the children with ASD, on the other hand, attended almost solely at either the left or the right part of the screen, supporting the previous conclusions and further demonstrating we can use this framework to understand attention shifting. In some embodiments, an example framework or system as described herein can utilize videos that swap regions that display the social and non-social stimuli during its presentation (e.g., halfway through video 200 social stimuli may be moved from a left region to a right region and non-social stimuli may be moved from the right region to the left region) to assess more fully what evokes attention shifts.

Hence, an example attention assessment framework and/or algorithm described herein can be used to explore and evaluate various attention dynamics, including patterns of attention shift as a result of stimulus changes, FIG. 8. While the actual population is relatively small in one or more studies described herein, differences can be seen depending on the screen region that is actually changing (e.g., a social or non-social region).

As discussed above, hypotheses previously derived from studies using state-of-the-art eye tracking technology were validated using an example attention assessment framework and/or algorithm described herein. In particular, attention assessment was performed for an ASD group and a control group and showed that the ASD users were more likely to have reduced attention to an attention assessment video (e.g., video 200) overall. Also, it was determined that while it was unlikely for a child without ASD to focus the majority of their attention on non-social stimuli, this occurred much more often among children with ASD. As such, this biomarker indicates a potential strong sensitivity as a risk marker for ASD. Further, it was determined that users with ASD are more likely to fixate on either part of an attention assessment video (e.g., a social or non-social region) than the non-ASD children, providing yet an additional potential biomarker.

While some aspects in the subject matter described herein relate to ASD (e.g., using stimuli and validation paradigms associated with ASD research literature), various aspects in the subject matter described herein can be utilized for various neuropsychiatric conditions beyond ASD, such as attention deficit and hyperactivity disorder (ADHD) and anxiety.

Figure 10:
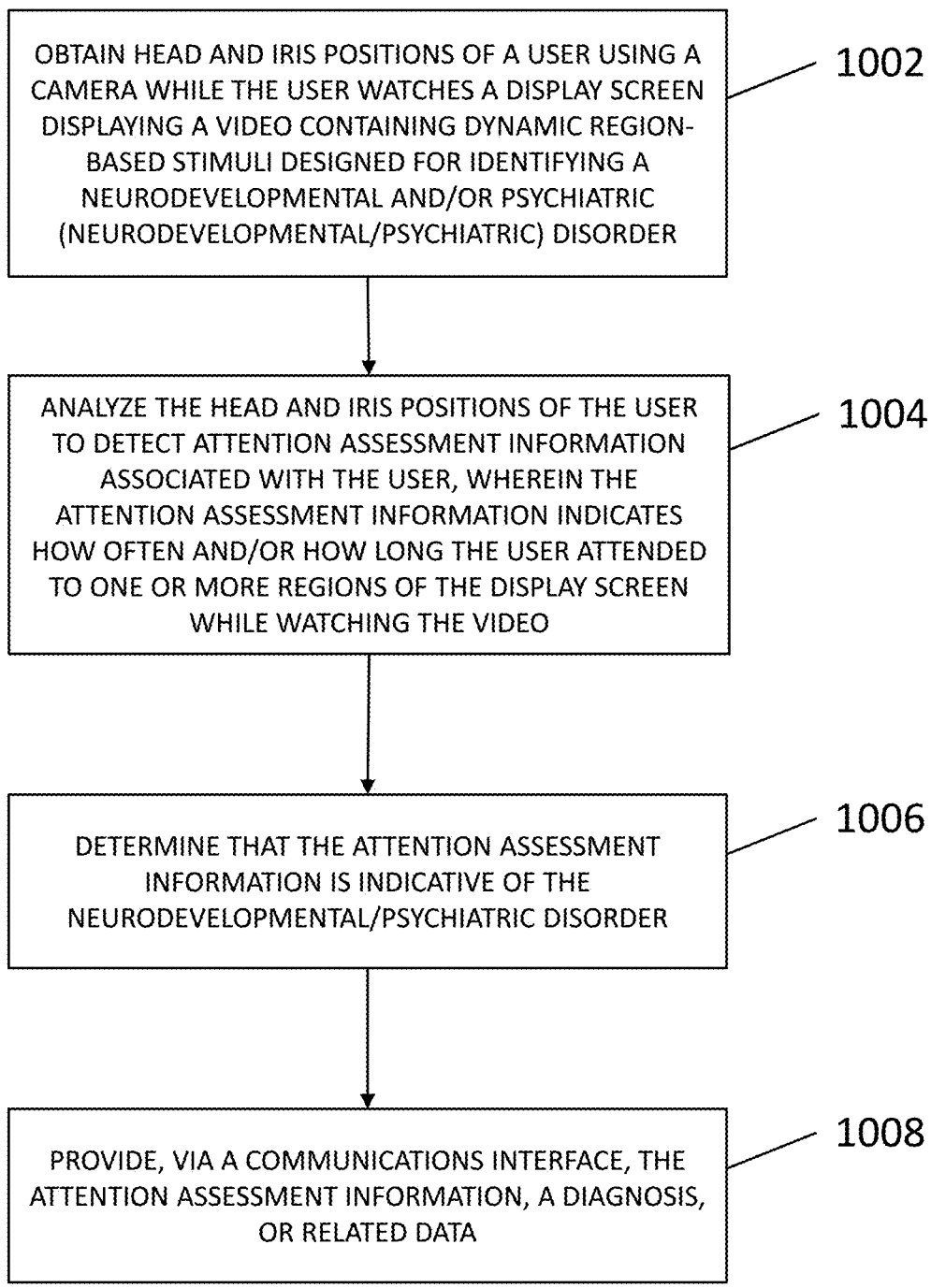
FIG. 10 is a diagram illustrating an example process for automated attention assessment.

FIG. 10 is a diagram illustrating an example process 1000 for automated attention assessment. In some embodiments, process 1000 described herein, or portions thereof, may be performed at or by computing platform 100, AAM 104, and/or another module or node. For example, computing platform 100 may be a mobile device, a computer, or other equipment (e.g., a computerized chair or room) and AAM 104 may include or provide an application running or executing on computing platform 100. In some embodiments, process 1000 may include steps 1002-1008.

In step 1002, head and iris positions of a user are obtained using a camera while the user watches a display screen displaying a video containing dynamic region-based stimuli designed for identifying a neurodevelopmental/psychiatric disorder.

In step 1004, the head and iris positions of the user may be analyzed to detect attention assessment information associated with the user, wherein the attention assessment information indicates how often and/or how long the user attended to one or more regions of the display screen while watching the video.

In step 1006, the attention assessment information may be determined to be indicative of the neurodevelopmental/psychiatric disorder.

In step 1008, the attention assessment information, a diagnosis, or related data may be provided via a communications interface.

In some embodiments, process 1000 may also include administering to the user an effective therapy for treating the neurodevelopmental/psychiatric disorder. For example, an attention assessment module executing on a smartphone may display one or more therapy or coping videos for improving a user's attention span for various types of stimuli (e.g., social stimuli).

In some embodiments, dynamic region-based stimuli may include a first region containing at least one social stimulus and a second region containing at least one non-social stimulus, wherein the at least one social stimulus may include at least one actor interacting with or appearing to interact with the user and wherein the at least one non-social stimulus may include at least one object moving or changing.

In some embodiments, obtaining head and iris positions of a user using a camera may include downloading or receiving images or a video recording of the user from the camera via wireless communication, electronic communication, or a storage device, wherein the camera may be located in the computing platform or is separate from the computing platform.

In some embodiments, analyzing head and iris positions of a user to detect attention assessment information associated with the user may comprise determining a direction of attention of the user for one or more frames or temporal blocks (time segments).

In some embodiments, determining a direction of attention of a user may include generating a midrange value of a yaw angle associated with the user based on a plurality of frames of a video; determining a yaw angle for a first head position of the user associated with a first frame of the plurality of frames; determining a first difference between the yaw angle for the first head position and the midrange value; determining a second difference between an extreme yaw angle associated with the first frame and the midrange value; determining whether the first difference is greater than the second difference by a first predetermined threshold value; and in response to determining that the first difference is greater than the second difference by the first predetermined threshold value, determining the direction of attention of the user is a first region of the display screen.

In some embodiments, a first predetermined threshold value may be ten percent or about ten percent.

In some embodiments, determining a direction of attention of a user may also include in response to determining that the first difference is not greater than the second difference by the first predetermined threshold value, using detected eye landmarks to determine the direction of attention of the user, wherein the direction of attention of the user may be determined to be one region of the display screen if a first distance between a center of the iris of an eye (e.g., landmark 304) and a center of the eye (e.g., based on landmarks 302 and 306) is larger than a computational result, wherein the computational result is determined by dividing a second distance between the center of the eye and an edge of the eye (e.g., landmark 302 or landmark 306) by a second predetermined threshold value.

In some embodiments, a second predetermined threshold value may be three or about three.

In some embodiments, a neurodevelopmental/psychiatric disorder may an ASD, an ADHD, or an anxiety disorder diagnosis.

In some embodiments, attention assessment information or related data may be provided to a user, a medical records system, a service provider, a healthcare provider, a system operator, a caregiver of the user, or any combination thereof. For example, e.g., where information is provided to a clinician or a medical professional, an attention assessment may include stimuli used in a test, recording of the user during the test, test results, and/or other technical or clinical information. In another example, e.g., where information is provided to a parent, an attention assessment may include a metric associated with an easy to understand scale (e.g., 0-100%) for indicating the likelihood of a user (e.g., a child) having a particular neurodevelopmental/psychiatric disorder and useful suggestions for improving one or more related symptoms associated with neurodevelopmental/psychiatric disorder.

In some embodiments, computing platform 100 may include a mobile device, a smartphone, a tablet computer, a laptop computer, a computer, an attention assessment device, or a medical device.

It will be appreciated that process 1000 is for illustrative purposes and that different and/or additional actions may be used. It will also be appreciated that various actions described herein may occur in a different order or sequence.

It should be noted that computing platform 100, AAM 104, and/or functionality described herein may constitute a special purpose computing device. Further, computing platform 100, AAM 104, and/or functionality described herein can improve the technological field of diagnosing and treating various neurodevelopmental/psychiatric disorders by providing mechanisms for automated attention assessment using videos designed for presenting region-based stimuli for facilitating detection of a viewer's direction of attention (e.g., left or right, up or down). Moreover, such mechanisms can alleviate many barriers, including costs, equipment, and human expertise, associated with conventional (e.g., clinical) methods of diagnosis and treatment of neurodevelopmental/psychiatric disorders.

The subject matter described herein for automated attention assessment improves the functionality of attention assessment devices and equipment by providing mechanisms (e.g., an automated attention assessment and/or tracking algorithm) that analyze a user's responses (e.g., head and eye positions of the user) to a video containing region-based stimuli. It should also be noted that computing platform 100 that implements subject matter described herein may comprise a special purpose computing device usable for various aspects of attention assessments, including videos containing region-based stimuli and/or gaze analysis.

The disclosure of each of the following references is incorporated herein by reference in its entirety to the extent not inconsistent herewith and to the extent that it supplements, explains, provides a background for, or teaches methods, techniques, and/or systems employed herein.

REFERENCES

1. Diagnostic and Statistical Manual of Mental Disorders, 4th Edn. American Psychiatric Association, 2000.
2. G. Dawson, A. Meltzoff, J. Osterling, J. Rinaldi, and E. Brown, "Children with autism fail to orient to naturally occurring social stimuli," Journal of Autism and Developmental Disorders, no. 28, pp. 479-485, 1998.
3. G. Dawson, K. Toth, R. Abbott, et al., "Early social attention impairments in autism: Social orienting, joint attention, and attention to distress," Developmental Psychology, no. 40(2), pp. 271-283, 2004.

4. K. Chawarska, S. Macari, and F. Shic, "Decreased spontaneous attention to social scenes in 6-month-old infants later diagnosed with autism spectrum disorders," Biological Psychiatry, no. 74(3), 195-203.
5. Klin, S. Shultz, and W. Jones, "Social visual engagement in infants and toddlers with autism: early developmental transitions and a model of pathogenesis," Neurosci Biobehav Rev., no. 50, pp. 189-203, 2014.
6. E. Werner, G. Dawson, J. Osterling, et al., "Brief report: Recognition of autism spectrum disorder before one year of age: a retrospective study based on home videotapes," Journal of Autism and Developmental Disorders, no. 30(2), pp. 157-162, 2000.
7. J. Constantino, S. Kennon-McGill, C. Weichselbaum, N. Marrus, A. Haider, A. Glowinski, S. Gillespie, C. Klaiman, A. Klin, and J. W., "Infant viewing of social scenes is under genetic control and is atypical in autism," Nature, vol. 547, pp. 340-344, July 2017.
8. Klin, W. Jones, R. Schultz, F. Volkmar, and D. Cohen, "Visual fixation patterns during viewing of naturalistic social situations as predictors of social competence in individuals with autism," V. Arch Gen Psychiatry, no. 59, pp. 809-816, 2002.
9. M. Murias, S. Major, K. Davlantis, L. Franz, A. Harris, B. Rardin, M. Sabatos-DeVito, and G. Dawson, "Validation of eye-tracking measures of social attention as a potential biomarker for autism clinical trials," Autism Res., no. 11(1), pp. 166-174, 2017.
10. C. Norbury, J. Brock, L. Cragg, S. Einav, H. Griffiths, and K. Nation, "Eye-movement patterns are associated with communicative competence in autistic spectrum disorders," Journal of Child Psychology and Psychiatry, no. 50(7), pp. 834-842, 2009.
11. K. Pierce, D. Conant, R. Hazin, R. Stoner, and J. Desmond, "Preference for geometric patterns early in life as a risk factor for autism," Archives of General Psychiatry, no. 68(1), pp. 101-109, 2011.
12. F. Shic, J. Bradshaw, A. Klin, B. Scassellati, and K. Chawarska, "Limited activity monitoring in toddlers with autism spectrum disorder," Brain Research, no. 1380, pp. 246-254, 2011.
13. J. Kirchner, A. Hatri, H. Heekeren, and I. Dziobek, "Autistic symptomatology, face processing abilities, and eye fixation patterns," Journal of Autism and Developmental Disorders, no. 41(2), pp. 158-167, 2011.
14. L. Shi, Y. Zhou, J. Ou, J. Gong, S. Wang, and X. Cui, "Different visual preference patterns in response to simple and complex dynamic social stimuli in preschool-aged children with autism spectrum disorders," PLOS ONE, no. 10(3), 2015.
15. J. Swettenham, S. Baron-Cohen, T. Charman, A. Cox, G. Baird, A. Drew, L. Rees, and S. Wheelwright, "The frequency and distribution of spontaneous attention shifts between social and nonsocial stimuli in autistic, typically developing, and nonautistic developmentally delayed infants," Journal of Child Psychology and Psychiatry, no. 39, pp. 747-753, 1998.
16. Y. Baveye, E. Dellandrea, C. Chamaret, and L. Chen, "LIRISACCEDE: a video database for affective content analysis," IEEE Transactions on Affective Computing, vol. 6, pp. 43-55, 2015.
17. N. Esler, V. Bal, W. Guthrie, A. Wetherby, S. Ellis Weismer, and C. Lord, "The Autism Diagnostic Observation Schedule, Toddler Module: Standardized severity scores," J Autism Dev Disord, vol. 45, pp. 2704-2720, 2015.
18. D. Robins, K. Casagrande, M. Barton, et al., "Validation of the modified checklist for autism in toddlers, revised with follow-up (m-chat-r/f)," PEDIATRICS, no. 133(1), pp. 37-45, 2014.
19. K. Campbell, K. Carpenter, S. Espinosa, et al., "Use of a digital modified checklist for autism in toddlers revised with followup to improve quality of screening for autism," The Journal of Pediatrics, no. 183, pp. 133-139, 2017.
20. J. Hashemi, K. Campbell, K. Carpenter, A. Harris, Q. Qiu, M. Tepper, S. Espinosa, J. Schaich-Borg, S. Marsan, R. Calderbank, J. Baker, H. Egger, G. Dawson, and G. Sapiro, "A scalable app for measuring autism risk behaviors in young children: A technical validity and feasibility study," MobiHealth, October 2015.
21. K. Gotham, S. Risi, A. Pickles, et al., "The autism diagnostic observation schedule: Revised algorithms for improved diagnostic validity," Journal of Autism and Developmental Disorders, no. 37(4), pp. 613-627, 2007.
22. E. Mullen, Mullen scales of early learning. Circle Pines, Minn.: American Guidance Service Inc, 1995.
23. "Duke A+ study: A research study for children between ages 1 and 7 years, https://autismcenter.duke.edu/research/dukestudy-research-study-children-between-ages-1-and-7-years,".
24. M. Murias, S. Major, S. Compton, J. Buttinger, J. Sun, J. Kurtzberg, and G. Dawson, "Electrophysiological biomarkers predict clinical improvement in an open-label trial assessing efficacy of autologous umbilical cord blood for treatment of autism," Stem Cells Translational Medicine, 2018.
25. K. Campbell, K. Carpenter, J. Hashemi, S. Espinosa, S. Marsan, J. Schaich-Borg, Z. Chang, W. Qiu, S. Vermeer, M. Tepper, J. Egger, J. Baker, G. Sapiro, and G. Dawson, "Computer vision analysis captures atypical social orienting in toddlers with autism," Autism: International Journal of Research and Practice, pp. 1-10, 2018.
26. E. J. Jones, K. Venema, R. Earl, R. Lowy, K. Barnes, A. Estes, G. Dawson, and S. Webb, "Reduced engagement with social stimuli in 6-month-old infants with later autism spectrum disorder: A longitudinal prospective study of infants at high familial risk," Journal of Neurodevelopmental Disorders, vol. 8, 2016.
27. F. De la Torre, W.-S. Chu, X. Xiong, et al., "Intraface," 11th IEEE International Conference and Workshops on Face and Gesture Recognition, pp. 1-8, 2015.
28. J. Hashemi, G. Dawson, K. Carpenter, K. Campbell, Q. Qiu, S. Espinosa, S. Marsan, J. Baker, H. Egger, and H. Sapiro, "Computer vision analysis for quantification of autism risk behaviours," IEEE Transactions on Affective Computing, 2018.
29. T. Baltruaitis, P. Robinson, and L.-P. Morency, "Openface: An open source facial behavior analysis toolkit," IEEE Winter Conference on Applications of Computer Vision (WACV), p. 110, 2016.
30. T. Baltruaitis, A. Zadeh, Y. Chong Lim, and L.-P. Morency, "Openface 2.0: Facial behavior analysis toolkit," IEEE International Conference on Automatic Face and Gesture Recognition, 2018.
31. M. Fischler and R. Bolles, "Random sample consensus: A paradigm for model fitting with applications to image analysis and automated cartography," Commun. ACM, no. 24(6), pp. 381-395, 1981.
32. M. Lucas da Silva, D. Goncalves, T. Guerreiro, and H. Silva, "A web-based application to address individual interests of children with autism spectrum disorders," Procedia Computer Science, vol. 14, pp. 20-27, 2012.

33. M. Lucas da Silva, H. Silva, and T. Guerreiro, "Inducing behavior change in children with autism spectrum disorders by monitoring their attention," Proceedings of the International Conference on Physiological Computing Systems, vol. 1, pp. 131-136, 2014.
34. O. Rudovic, J. Lee, M. Dai, B. Schuller, and R. Picard, "Personalized machine learning for robot perception of affect and engagement in autism therapy," Science Robotics, vol. 3:19, June 2018.
35. K. Pelphrey, N. Sasson, S. Reznick, G. Paul, B. Goldman, and J. Piven, "Visual scanning of faces in autism," Journal of Autism and Developmental Disorders, vol. 32, no. 4, pp. 249-61, 2002.
36. N. Merin, G. Young, S. Ozonoff, and S. Rogers, "Visual fixation patterns during reciprocal social interaction distinguish a subgroup of 6-month-old infants at risk for autism from comparison infants," J Autism Dev Disord, no. 37, pp. 108-121, 2006.
37. H. Egger, G. Dawson, J. Hashemi, K. Carpenter, S. Espinosa, K. Campbell, S. Brotkin, J. Shaich-Borg, Q. Qiu, M. Tepper, J. Baker, R. Bloomfield, and G. Sapiro, "Automatic emotion and attention analysis of young children at home: A researchkit autism feasibility study," npj Nature Digital Medicine, June 2018.
38. G. Dawson, K. Campbell, J. Hashemi, S. Lippmann, V. Smith, K. Carpenter, H. Egger, S. Espinosa, S. Vermeer, J. Baker, and G. Sapiro, "Atypical postural control can be detected via computer vision analysis in toddlers with autism spectrum disorder," 2018, under review.
39. Q. Qiu et al., "Low-cost gaze and pulse analysis using realsense," MobiHealth, 2015.
40. Z. Chang, Q. Qiu, and G. Sapiro, "Synthesis-based low-cost gaze analysis," International Conference on Human-Computer Interaction, July 2016.

It will be understood that various details of the subject matter described herein may be changed without departing from the scope of the subject matter described herein. Furthermore, the foregoing description is for the purpose of illustration only, and not for the purpose of limitation, as the subject matter described herein is defined by the claims as set forth hereinafter.

What is claimed is:

1. A method for automated attention assessment, the method comprising:
    at a computing platform including at least one processor and memory:
        obtaining head and iris positions of a user using a camera while the user watches a display screen displaying a video containing dynamic region-based stimuli designed for identifying a neurodevelopmental and/or psychiatric (neurodevelopmental/psychiatric) disorder, wherein the dynamic region-based stimuli includes a first region containing at least one social stimulus and a second region containing at least one non-social stimulus, wherein the at least one social stimulus includes at least one actor interacting with or appearing to interact with the user and wherein the at least one non-social stimulus includes at least one object moving or changing;
        analyzing the head and iris positions of the user to detect attention assessment information associated with the user, wherein the attention assessment information indicates how often and/or how long the user attended to one or more of the regions of the display screen while watching the video;
        determining that the attention assessment information is indicative of the neurodevelopmental/psychiatric disorder; and
        providing, via a communications interface, the attention assessment information, a diagnosis, or related data.

2. The method of claim 1 comprising:
    administering to the user an effective therapy for treating the neurodevelopmental/psychiatric disorder.

3. The method of claim 1 wherein obtaining the head and iris positions of the user using the camera includes downloading or receiving images or a video recording of the user from the camera via wireless communication, electronic communication, or a storage device, wherein the camera is located in the computing platform or is separate from the computing platform.

4. The method of claim 1 wherein analyzing the head and iris positions of the user to detect attention assessment information associated with the user comprises determining a direction of attention of the user, wherein determining the direction of attention of the user comprises:
    generating a midrange value of a yaw angle associated with the user based on a plurality of frames of the video;
    determining a yaw angle for a first head position of the user associated with a first frame of the plurality of frames;
    determining a first difference between the yaw angle for the first head position and the midrange value;
    determining a second difference between an extreme yaw angle associated with the first frame and the midrange value;
    determining whether the first difference is greater than the second difference by a first predetermined threshold value; and
    in response to determining that the first difference is greater than the second difference by the first predetermined threshold value, determining the direction of attention of the user is a first region of the display screen.

5. The method of claim 4 comprising:
    in response to determining that the first difference is not greater than the second difference by the first predetermined threshold value, using detected eye landmarks to determine the direction of attention of the user, wherein the direction of attention of the user is determined to be one region of the display screen if a first distance between a center of the iris of an eye and a center of the eye is larger than a computational result, wherein the computational result is determined by dividing a second distance between the center of the eye and an edge of the eye by a second predetermined threshold value.

6. The method of claim 5 wherein the first predetermined threshold value is ten percent and wherein the second predetermined threshold value is three.

7. The method of claim 1 wherein the neurodevelopmental/psychiatric disorder comprises autism spectrum disorder (ASD), an attention deficit and hyperactivity disorder (ADHD), or an anxiety disorder diagnosis.

8. The method of claim 1 wherein the computing platform includes a mobile device, a smartphone, a tablet computer, a laptop computer, a computer, an attention assessment device, or a medical device.

9. A system for automated attention assessment, the system comprising:
    a computing platform including at least one processor and memory, the computing platform including:

wherein the computing platform is configured for:
obtaining head and iris positions of a user using a camera while the user watches a display screen displaying a video containing dynamic region-based stimuli designed for identifying a neurodevelopmental and/or psychiatric (neurodevelopmental/psychiatric) disorder, wherein the dynamic region-based stimuli includes a first region containing at least one social stimulus and a second region containing at least one non-social stimulus, wherein the at least one social stimulus includes at least one actor interacting with or appearing to interact with the user and wherein the at least one non-social stimulus includes at least one object moving or changing;
analyzing the head and iris positions of the user to detect attention assessment information associated with the user, wherein the attention assessment information indicates how often and/or how long the user attended to one or more of the regions of the display screen while watching the video;
determining that the attention assessment information is indicative of the neurodevelopmental/psychiatric disorder; and
providing, via a communications interface, the attention assessment information, a diagnosis, or related data.

10. The system of claim 9 wherein the computing platform or another entity administers to the user an effective therapy for treating the neurodevelopmental/psychiatric disorder.

11. The system of claim 9 wherein the computing platform is configured for downloading or receiving images or a video recording of the user from the camera via wireless communication, electronic communication, or a storage device, wherein the camera is located in the computing platform or is separate from the computing platform.

12. The system of claim 9 wherein the computing platform is configured for determining a direction of attention of the user comprising:
generating a midrange value of a yaw angle associated with the user based on a plurality of frames of the video;
determining a yaw angle for a first head position of the user associated with a first frame of the plurality of frames;
determining a first difference between the yaw angle for the first head position and the midrange value;
determining a second difference between an extreme yaw angle associated with the first frame and the midrange value;
determining whether the first difference is greater than the second difference by a first predetermined threshold value; and
in response to determining that the first difference is greater than the second difference by the first predetermined threshold value, determining the direction of attention of the user is a first region of the display screen.

13. The system of claim 12 comprising:
in response to determining that the first difference is not greater than the second difference by the first predetermined threshold value, using detected eye landmarks to determine the direction of attention of the user, wherein the direction of attention of the user is determined to be one region of the display screen if a first distance between a center of the iris of an eye and a center of the eye is larger than a computational result, wherein the computational result is determined by dividing a second distance between the center of the eye and an edge of the eye by a second predetermined threshold value.

14. The system of claim 13 wherein the first predetermined threshold value is ten percent and wherein the second predetermined threshold value is three.

15. The system of claim 9 wherein the neurodevelopmental/psychiatric disorder comprises autism spectrum disorder (ASD), an attention deficient and hyperactivity disorder (ADHD), or an anxiety disorder diagnosis.

16. The system of claim 9 wherein the computing platform includes a mobile device, a smartphone, a tablet computer, a laptop computer, a computer, an attention assessment device, or a medical device.

17. A non-transitory computer readable medium comprising computer executable instructions embodied in a computer readable medium that when executed by at least one processor of a computer cause the computer to perform steps comprising:
obtaining head and iris positions of a user using a camera while the user watches a display screen displaying a video containing dynamic region-based stimuli designed for identifying a neurodevelopmental and/or psychiatric (neurodevelopmental/psychiatric) disorder, wherein the dynamic region-based stimuli includes a first region containing at least one social stimulus and a second region containing at least one non-social stimulus, wherein the at least one social stimulus includes at least one actor interacting with or appearing to interact with the user and wherein the at least one non-social stimulus includes at least one object moving or changing;
analyzing the head and iris positions of the user to detect attention assessment information associated with the user, wherein the attention assessment information indicates how often and/or how long the user attended to one or more of the regions of the display screen while watching the video;
determining that the attention assessment information is indicative of the neurodevelopmental/psychiatric disorder; and
providing, via a communications interface, the attention assessment information, a diagnosis, or related data.

18. The non-transitory computer readable medium of claim 17 comprising:
administering to the user an effective therapy for treating the neurodevelopmental/psychiatric disorder.

* * * * *